(12) United States Patent
Sasaki et al.

(10) Patent No.: US 7,635,422 B2
(45) Date of Patent: Dec. 22, 2009

(54) ELECTRODE PLATE FOR ELECTROCHEMICAL MEASUREMENTS

(75) Inventors: Hidehiro Sasaki, Osaka (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/436,418

(22) Filed: May 6, 2009

(65) Prior Publication Data

US 2009/0211922 A1    Aug. 27, 2009

Related U.S. Application Data

(63) Continuation of application No. PCT/JP2008/002549, filed on Sep. 17, 2008.

(30) Foreign Application Priority Data

Nov. 1, 2007    (JP)    ............................. 2007-285070

(51) Int. Cl.
  *G01N 27/30*    (2006.01)
(52) U.S. Cl. .................... 205/775; 205/777.5; 204/400; 204/403.01; 204/411
(58) Field of Classification Search ................ 204/400, 204/403.01, 409, 411; 205/775, 777.5
See application file for complete search history.

(56) References Cited

U.S. PATENT DOCUMENTS 6,835,293 B2 * 12/2004 Gerlach et al. .............. 204/600

FOREIGN PATENT DOCUMENTS

EP    0 569 908 A2    11/1993

(Continued)

OTHER PUBLICATIONS

Horiuchi, T., et al., "Limiting Current Enhancement by Self-Induced Redox Cycling on a Micro-Macro Twin Electrode", J. Electrochem. Soc, Dec. 1991, pp. 3549-3553, vol. 138 No. 12, The Electrochemical Society, Inc.

(Continued)

*Primary Examiner*—Kaj K Olsen
(74) *Attorney, Agent, or Firm*—McDermott Will & Emery LLP

(57) ABSTRACT

An electrode plate for electrochemical measurements capable of measuring the concentration of a target substance included in a sample solution with favorable accuracy and high sensitivity is provided. The electrode plate for electrochemical measurements of the present invention includes a substrate, an upper layer, a lower layer, a first electrode body sandwiched between the substrate and the upper layer, and a second electrode body sandwiched between the substrate and the lower layer, wherein: the upper layer has a plurality of upper layer through-holes; the first electrode body has a plurality of first electrodes exposed from via the upper layer through-hole in the first electrode body; the substrate has a plurality of substrate through-holes; and the second electrode body has a plurality of second electrodes exposed via the upper layer through-hole and the substrate through-hole in the second electrode body.

24 Claims, 18 Drawing Sheets

FOREIGN PATENT DOCUMENTS

| | | |
|---|---|---|
| JP | 02-268265 | 11/1990 |
| JP | 03-179248 | 8/1991 |
| JP | 03-238350 | 10/1991 |
| JP | 03-505785 | 12/1991 |
| JP | 04-136748 | 5/1992 |
| JP | 06-027081 | 2/1994 |
| JP | 3289059 | 3/2002 |
| JP | 2006-078404 | 3/2006 |
| JP | 2007-010429 | 1/2007 |
| WO | WO 90/12314 | 10/1990 |

OTHER PUBLICATIONS

Koichi Aoki, et al., "Electrochemical Measurement Method Using Microelectrode", edited by The Institute of Electronics, Information and Communication Engineers, published on Feb. 10, 1998, pp. 48-49 and 70-71.

* cited by examiner (a)

(b)

ELECTRODE PLATE FOR ELECTROCHEMICAL MEASUREMENTS

This Application is a continuation of International Application No. PCT/JP2008/002549, whose international filing date is Sep. 17, 2008 which in turn claims the benefit of Japanese Patent Application No. 2007-285070, filed on Nov. 1, 2007, the disclosures of which Applications are incorporated by reference herein. The benefit of the filing and priority dates of the International and Japanese Applications is respectfully requested.

BACKGROUND OF THE INVENTION

1. Field of the Invention

The present invention relates to an electrode plate for electrochemical measurements for detecting with high sensitivity and determining quantitatively a substance included in a living body in a slight amount.

2. Related Art

In recent years, electrode plates for electrochemical measurements for quantitatively determining a saccharide such as sucrose, glucose or the like included in blood by a combination of a specific catalytic action of an enzyme and an electronic mediator having an electrode reaction activity have been developed.

According to such an electrode plate for electrochemical measurements, after the reaction is allowed between the saccharide and the enzyme, the electronic mediator is electrochemically measured, whereby the saccharide included in the sample solution is quantitatively determined indirectly via the electronic mediator.

This method is highly specific for the saccharide, accompanied by less influences from the temperature during operation, and the mechanism of the quantitative analysis unit is simple; therefore, ordinary persons can quantitatively determine the saccharide easily at home and the like by using this method.

The electrode plate for electrochemical measurements is suited for analyses of solution samples of a slight amount included in living bodies. Thus, applications of the electrode plate for electrochemical measurements have been attempted to sensors and the like through combining with a variety of organic materials or inorganic materials. The electrode response speed of the electrode plate for electrochemical measurements is accelerated as the area of a microelectrode carried by the electrode plate for electrochemical measurements is reduced. Therefore, various electrode shapes, and miniaturization of electrodes have been investigated.

However, as the area of the electrode is reduced, the resulting electric current value is lowered. For example, when the area of the electrode is miniaturized to approximately several hundred $\mu m^2$, detectable electric current value may be lowered to several ten to several nA order. Thus, increase in noise response, and deterioration of the sensitivity may be caused in measurement. Accordingly, in order to avoid these defects, electrode plates for electrochemical measurements in which a plurality of microelectrodes are integrated were studied as in Patent Documents 1 to 4.

In Patent Documents 1 to 4, methods of producing a large quantity of microelectrodes on a substrate while keeping a constant distance between adjacent microelectrodes with favorable reproducibility are proposed.

FIG. 17 shows an overall view (FIG. 17(a)) and a partial enlarged view (FIG. 17(b)) of the construction of a conventional electrode plate for electrochemical measurements disclosed in Patent Document 1. This electrode plate for electrochemical measurements 200 is constructed by laminating insulative substrate 201/bottom electrode body 202 that functions as an oxidation electrode/insulating layer 203/surface electrode 204 that functions as a reduction electrode. A large number of cylindrical micropores 5 are formed on the surface of the surface electrode 204, and the film face of the bottom electrode body 202 is exposed to the micropore 5.

The insulative substrate 201 is constituted with, for example, a silicon substrate with an oxide film, generally referred to, in which oxide film 201b is adhered on the main surface of silicon substrate 201a. The bottom electrode body 202 is an oxidation electrode formed with a metal, a semimetal, a carbonic material, or a semiconductor on the surface of the oxide film 201b of the substrate 201 (i.e., insulator surface). The surface electrode 204 is a reduction electrode formed with a metal, a semimetal, or a semiconductor on the insulating layer 203, similarly to the bottom electrode body 202. A working electrode pair is formed with an exposed part of the bottom electrode body 202 from micropore 5 (hereinafter, referred to as oxidation electrode 202), and the surface electrode 204. In other words, both the oxidation electrode 202a and the surface electrode 204 function as working electrodes, and more specifically, the exposed part of the bottom electrode body 202 functions as an oxidation electrode, while the surface electrode 204 functions as a reduction electrode, as described above. In FIG. 17, the reference numeric character 207 represents an opening for drawing the electrode, opened so as to connect an outer lead to one end of the bottom electrode body 202. Herein, the micropore 205 represents a hole that completely penetrates through the insulating layer 203 and the surface electrode 204, and then reaches to the surface of the bottom electrode body 202.

In an apparatus for electrochemical measurements in which the electrode plate for electrochemical measurements as described above is used, a potential is applied to the bottom electrode body 202 and the surface electrode 204 for achieving an electric current response. When the apparatus for electrochemical measurements is constructed with three electrodes, i.e., the oxidation electrode body 202a, surface electrode 204, and a counter electrode (not shown in the Figure), a potential is applied between the oxidation electrode body 202a and the counter electrode, and between the surface electrode 204 and the counter electrode, provided that the potential shown by the counter electrode in the sample solution is zero. In addition, when the apparatus for electrochemical measurements is constructed with four electrodes, i.e., the oxidation electrode body 202a, surface electrode 204, a reference electrode (not shown in the Figure), and an auxiliary electrode (not shown in the Figure), a potential is applied between the oxidation electrode body 202a and the reference electrode, and between the surface electrode 204 and the reference electrode, provided that the potential shown by the reference electrode in the sample solution is zero.

In Patent Document 4 and Nonpatent Document 1, an electrode plate for electrochemical measurements is proposed in which cylindrical micropores 205 are provided such that the intervals among them becomes greater than their diameter, and the results of electrochemical measurements using the same are reported. In these Documents, the surface electrode 204 that is a macroelectrode has an area greater than the bottom electrode that is an assembly of microelectrodes. Upon measurement, potentials are applied, respectively, which can cause an oxidative reaction on the oxidation electrode body 202a, and a reductive reaction on the surface electrode 204. It is reported that self-induced redox cycle is thus generated between the oxidation electrode body 202a and the surface electrode 204, whereby apparently high electric current response can be achieved.

In this manner, a target substance such as a saccharide is quantitatively determined via an electronic mediator that is present in a sample solution.

Alternatively, even though a potential that causes a reductive reaction is applied on the oxidation electrode body 202a, while a potential that causes an oxidative reaction is applied on the surface electrode 204, similar self-induced redox cycle is generated.

Hereinbelow, the self-induced redox cycle described in Patent Document 4, and Nonpatent Documents 1 and 2 is explained with reference to FIG. 18.

The self-induced redox cycle in FIG. 18 proceeds on two working electrodes, i.e., microelectrode 221 and macroelectrode 222.

An oxidative reaction of reductant 224 is caused to produce oxidant 225 on the surface of the microelectrode 221, whereby an oxidation current flows to the microelectrode 221.

On the surface of a part 222a, which is close to the microelectrode 221, of the macroelectrode 222, the oxidant 225 is reduced to be converted into reductant 226, whereby a reductive electric current flows to the macroelectrode 222.

Furthermore, the reductant 225 is diffused to reach to the surface of the microelectrode 221, whereby an oxidative reaction is caused again from the reductant 224 to the oxidant 225, leading to an oxidation current to flow toward the microelectrode 221. As a consequence, the reductant 224 can be fed to the surface of the microelectrode 221 by reducing the oxidant 225 generated from the microelectrode 221 to give the reductant 226 on the surface of the macroelectrode 222a.

Accordingly, as a result of occurrence a so-called redox cycle reaction in which an oxidative reaction and a reductive reaction recur between the microelectrode 221 and the macroelectrode 222a, an electric current constantly flows to the microelectrode 221, and thus the target substance included in a sample solution in a slight amount can be detected and quantitatively determined.

Moreover, in order to improve the efficacy of the measurement with high sensitivity, electrode pairs consisting of an oxidation electrode and a reduction electrode by which a redox cycle proceeds are formed as many as possible through forming a larger number of the microelectrodes 221 on the substrate.

Patent Document 1: Japanese Patent No. 2556993 (page 6, FIG. 1)

Patent Document 2: Japanese Patent No. 2564030 (page 7, FIG. 2)

Patent Document 3: Japanese Unexamined Patent Application, First Publication No. 2006-78404 (column 25, FIG. 1)

Patent Document 4: Japanese Patent No. 3289059 (page 16, FIG. 5)

Patent Document 5: Japanese Unexamined Patent Application, First Publication No. 2007-010429 (FIG. 3, FIG. 4)

Nonpatent Document 1: J. Electrochem. Soc., Vol. 138, No. 12, page 3551

Nonpatent Document 2: Koichi Aoki et al., "Electrochemical Measurement Method Using Microelectrode" edited by The Institute of Electronics, Information and Communication Engineers, published on Feb. 10, 1998 pages 48-49 and 70-71

SUMMARY OF THE INVENTION

As shown in FIG. 17, when the area of the surface electrode 204 that functions as a reduction electrode is much greater than the area of oxidation electrode 202a, problems as in the following are caused.

Although reductant 226 formed on macroelectrode 222a is diffused, it reaches not only to the microelectrode 221 (corresponding to oxidation electrode body 202a in FIG. 17), but in part, also onto a part 222b, which is far from the microelectrode 221, of the macroelectrode 222 (corresponding to surface electrode 204 in FIG. 17) as shown in FIG. 18, right side. Such a reductant 227 is converted in to oxidant 228 by an oxidative reaction. In other words, an oxidative reaction is also caused on the macroelectrode 222 (see, also FIG. 4 in Japanese Unexamined Patent Application, First Publication No. Hei 3-246460).

Next, the oxidant 228 is diffused, and reaches onto a part 222a, which is close to the microelectrode 221, of the macroelectrode 222. The reductant 226 is yielded there by a reductive reaction. The reductant 226 is diffused, reaches onto the surface of the microelectrode 221, and oxidized again to be converted into oxidant 225 (alternatively, reaches again to a part 222b, which is far from the microelectrode 221, of the macroelectrode 222).

Accordingly, on the surface electrode 204 shown in FIG. 17, an oxidative reaction occurs concurrently with a reductive reaction. As a result, oxidation of the reductant, the detection of which should be effected on the oxidation electrode body 202a, is also caused on the surface electrode 204 concomitantly.

Therefore, the reductant generated on the surface electrode 204 is not oxidized efficiently on the oxidation electrode body 202a, thereby leading to problems in improvement of sensitivity.

In addition, since the surface electrode 204 operates as a macroelectrode, a great charge current is achieved in applying the potential. Thus, a problem of lengthening of the time required until the reaction reaches to a stationary state as compared with the oxidation electrode body 202a that is a microelectrode has also caused.

The present invention was made in order to solve the problems described above, and an object of the invention is to provide an electrode plate for electrochemical measurements which can carry out quantitative determination or quantitative measurement of the concentration of a target substance such as a saccharide included in a sample solution via an electronic mediator with favorable accuracy and high sensitivity.

In order to solve the foregoing problems, the electrode plate for electrochemical measurements of the present invention includes a substrate made of an insulator, an upper layer made of an insulator provided on the superior face of the substrate, a lower layer made of an insulator provided on the inferior face of the substrate, a first electrode body sandwiched between the superior face of the substrate and the upper layer, and a second electrode body sandwiched between the inferior face of the substrate and the lower layer, wherein: the upper layer has a plurality of upper layer through-holes; the first electrode body has a plurality of first electrodes comprising a portion exposed from the superior face of the upper layer via the upper layer through-hole in the first electrode body; the substrate has a plurality of substrate through-holes; and the second electrode body has a plurality of second electrodes comprising a portion exposed from the superior face of the upper layer via the upper layer through-hole and the substrate through-hole in the second electrode body in the second electrode body, and wherein: on a plane view, any of the plurality of substrate through-holes does not overlap with the first electrode body; four second electrodes are disposed around the each first electrode, with an even distance between centers of the first electrode and the second electrode; four first electrodes are disposed around the each second electrode, with an even distance between centers of the second electrode and the first electrode, the area of the each first electrode is all substantially the same as the area of the each second electrode.

In one embodiment of the present invention, the first electrode body includes a plurality of branches that form zigzag extended such that the first electrodes are serially linked, and a stem to which one end of the plurality of branches is connected.

In one embodiment of the present invention, the second electrode body includes a plurality of branches that form zigzag extended such that the second electrodes are serially linked, and a stem to which one end of the plurality of branches is connected.

In one embodiment of the present invention, the first electrode body is constituted with a metal plate having a plurality of cut-part formed by cutting off to be slightly larger than regions corresponding to the plurality of substrate through-holes.

In one embodiment of the present invention, the second electrode body is constituted with a metal plate including all the plurality of second electrodes.

In the electrode plate for electrochemical measurements of the present invention, preferably, the cross sectional area of the each upper layer through-hole is substantially the same as the area of the each first electrode, and the cross sectional area of the each substrate through-hole is substantially the same as the area of the each second electrode.

In one embodiment of the present invention, the cross-sectional shape of the each upper layer through-hole and the cross-sectional shape of the each substrate through-hole are a regular tetragon.

In one embodiment of the present invention, the cross-sectional shape of the each upper layer through-hole and the cross-sectional shape of the each substrate through-hole are a regular hexagon.

Furthermore, the electrode plate for electrochemical measurements is combined with either a reference electrode and an auxiliary electrode, or a counter electrode, whereby an apparatus for electrochemical measurements is constructed. This apparatus for electrochemical measurements is also involved in principles the present invention.

In addition, a method of the quantitative determination of a target substance included in a sample solution containing an electronic mediator with this apparatus for electrochemical measurements as described in the following is also involved in the principles of the present invention. The method of the quantitative determination of a target substance according to the present invention includes the steps of: bringing the reference electrode, the auxiliary electrode, and the electrode plate for electrochemical measurements, or the counter electrode and the electrode plate for electrochemical measurements into contact with the sample solution; measuring the electric current by sweeping a positive potential to either one of the first electrode body and the second electrode body, and applying a negative potential to another one, or applying a positive potential to either one of the first electrode body and the second electrode body, and sweeping a negative potential to another one, thereby determining the electric current that flows between the first electrode body and the second electrode body; and calculating the amount of the target substance from the electric current derived in the step of measuring the electric current.

The aforementioned and other objects, features, and advantages of the present invention are clarified by the following detailed description of preferred embodiments with reference to accompanying drawings.

According to the present invention, the concentration of a target substance included in a sample can be measured with favorable accuracy and high sensitivity.

DETAILED DESCRIPTION OF THE INVENTION

Hereinafter, preferred embodiments of the present invention are explained with reference to accompanying drawings.

First Embodiment

Figure 1:
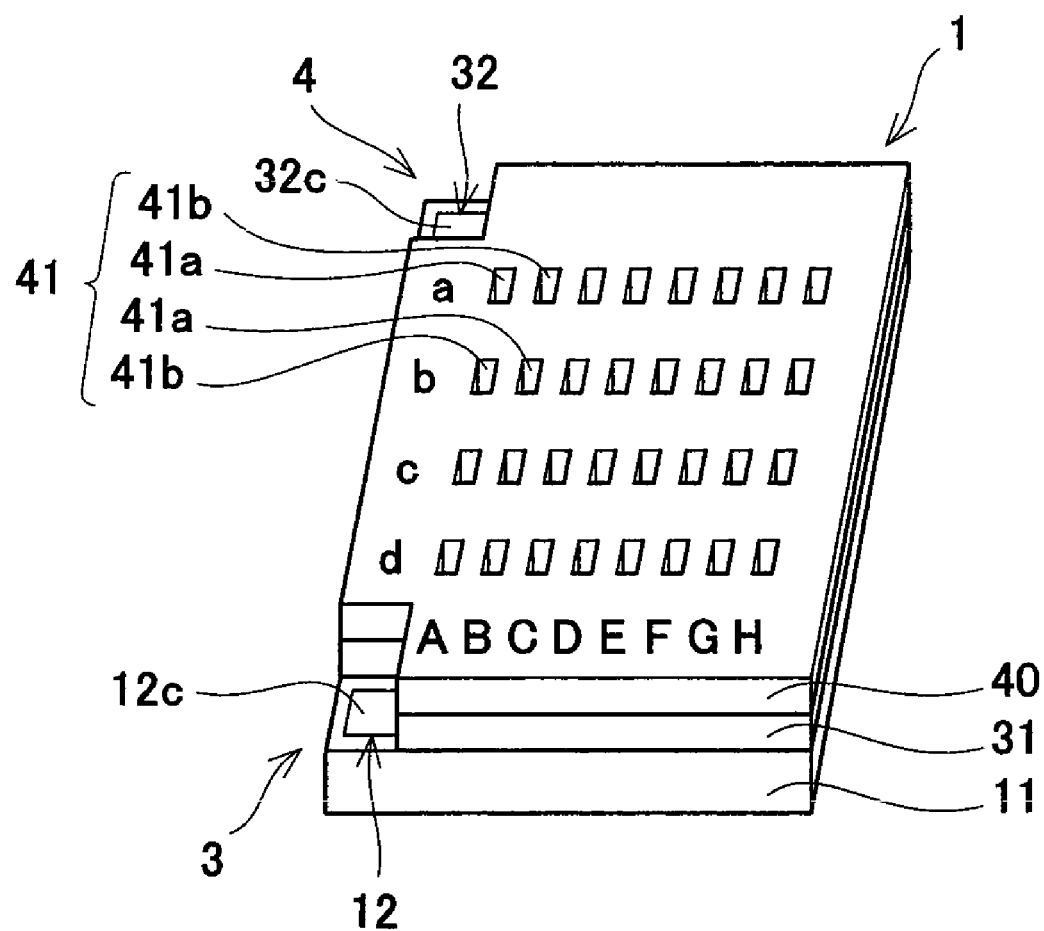
FIG. 1 shows a perspective view schematically illustrating an electrode plate for electrochemical measurements according to the first embodiment.

FIG. 1 shows a perspective view schematically illustrating the electrode plate for electrochemical measurements according to the first embodiment. In the construction of electrode plate for electrochemical measurements 1, lower layer 11, substrate 31, and upper layer 40 are laminated in this order from the under side, with oxidation electrode body 12 being sandwiched between the lower layer 11 and the substrate 31, and with reduction electrode body 32 being sandwiched between the substrate 31 and the upper layer 40. On the upper layer 40, a plurality of upper layer through-holes 41 are formed to give a matrix shape. More specifically, the upper layer through-holes 41 in the total number of thirty two are formed, 8 columns along the lateral direction, and 4 lines along the lengthwise direction. Each upper layer through-hole 41 has a cross-sectional shape of regular tetragon, and further the upper layer through-holes 41b that allow the reduction electrode body 32 to be exposed to the superior face of the electrode plate for electrochemical measurements 1, and the upper layer through-holes 41a that allow the oxidation electrode body 12 to be exposed to the superior face of the electrode plate for electrochemical measurements 1 are alternately disposed at regular intervals. The upper layer through-holes 41a allow the oxidation electrode body 12 to be exposed to the superior face of the electrode plate for electrochemical measurements 1 via the substrate through-hole on the substrate 31 not shown in FIG. 1. On the plane view, positions where the upper layer through-holes 41 are formed in the lateral direction are designated A, B, C, D, . . . and H in sequence, and positions in the lengthwise direction are designated as a, b, c and d in sequence. Additionally, upper layer through-hole 41 (X, x) represents the upper layer through-hole 41 situated at X (X=A, B, C, D, . . . , H) in the lateral direction, and at x (x=a, b, c, d) in the lengthwise direction.

The electrode plate for electrochemical measurements 1 has: notch 3 which is formed such that oxidation electrode lead 12c provided as a member of the oxidation electrode body 12 is exposed in the vicinity of the end, and notch 4 which is formed such that reduction electrode lead 32c provided as a member of the reduction electrode body 32 is exposed in the vicinity of the end.

Figure 2:
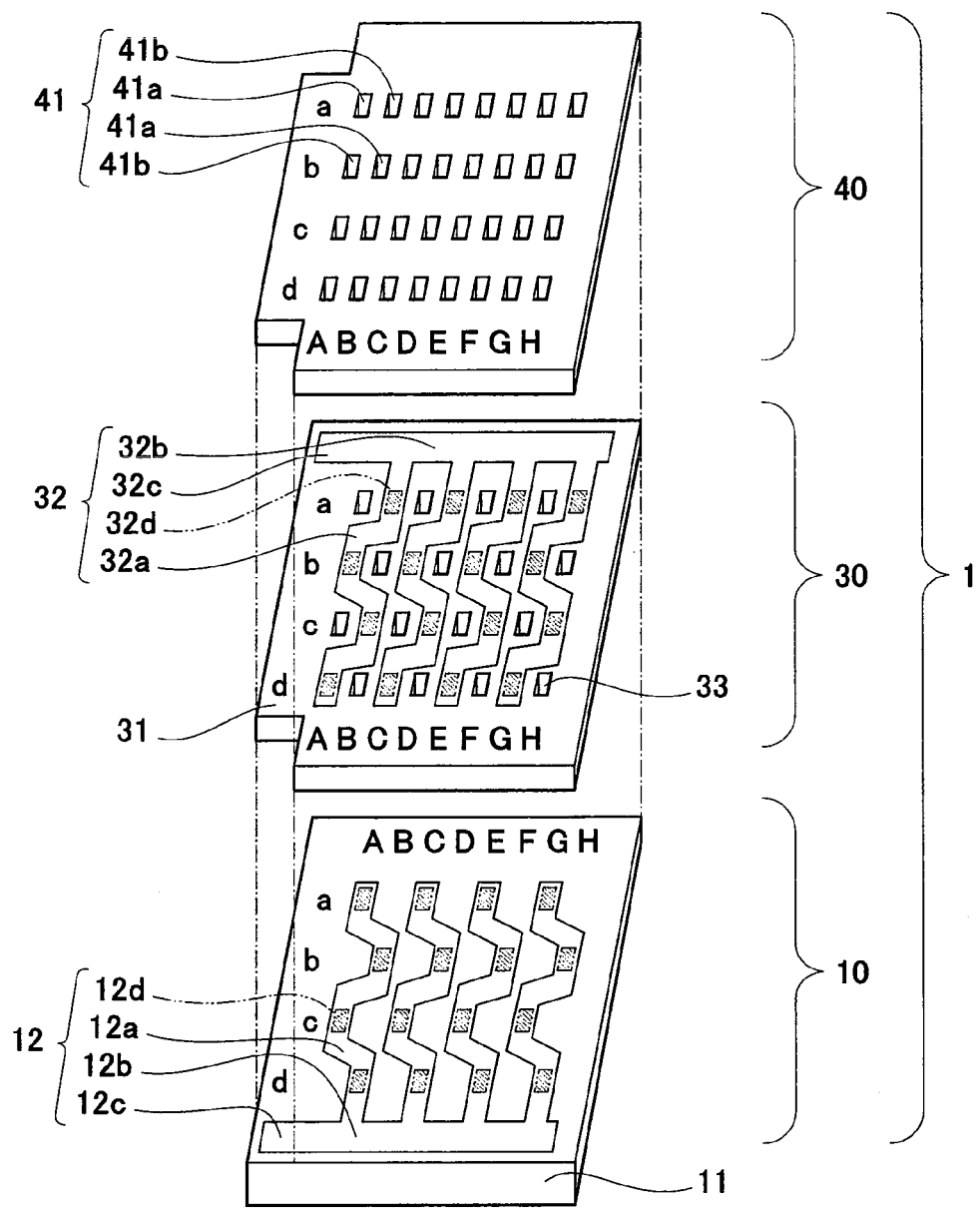
FIG. 2 shows an exploded perspective view schematically illustrating the electrode plate for electrochemical measurements according to the first embodiment.

FIG. 2 shows an exploded perspective view illustrating the electrode plate for electrochemical measurements 1 shown in FIG. 1. As is shown in FIG. 2, in the electrode plate for electrochemical measurements 1 according to the first embodiment, oxidation electrode-mounted layer 10, reduction electrode-mounted layer 30, and upper layer 40 are laminated in this order from the under side. The oxidation electrode-mounted layer 10 is constituted with lower layer 11 and oxidation electrode body 12 provided on the superior face of the lower layer 11. The reduction electrode-mounted layer 30 is constituted with substrate 31 and oxidation electrode body 32 provided onto the superior face of the substrate 31. The lower layer 11, the substrate 31, and the upper layer 40 are all insulators.

The oxidation electrode body 12 is sandwiched between the lower layer 11 and the substrate 31 as shown in FIG. 2. Similarly, the reduction electrode body 32 is sandwiched between the substrate 31 and the upper layer 40.

The upper layer 40 has a plurality of upper layer through-holes 41. In FIG. 2, thirty two upper layer through-holes 41 are provided. A part of the reduction electrode body 32 is exposed from the upper layer through-hole 41b (a, B) at the right side of the upper layer through-hole 41a (a, A) positioned at the upper left, and every other through-holes 41b in the lengthwise direction and the lateral direction with this upper layer through-hole 41b as a base point, among the thirty two upper layer through-holes 41. Of the reduction electrode body 32, the parts exposed from each upper layer through-hole 41a, i.e., hatched portions on the oxidation electrode body 32 in FIG. 2 are brought into contact with the sample solution, and functions as reduction electrode 32d. In FIG. 2, sixteen reduction electrodes 32d are provided. Of the reduction electrode body 32, the part on which the upper layer 40 is formed, i.e., a part unhatched without printed designation on the reduction electrode body 32 in FIG. 2 is not to be in contact with the sample solution. Thus, this part does not function as a reduction electrode. The reduction electrode body 32 includes a plurality of branches 32a having a zigzag shape extended in the lengthwise direction while sequentially linking the parts exposed from the upper layer through-hole 41b alternately on the adjacent two columns, and stem 32b that is connected to one end of all branches 32a. In addition, the reduction electrode body 32 has reduction electrode lead 32c at one end of the stem 32b.

The substrate 31 has a plurality of substrate through-holes 33. In FIG. 2, sixteen substrate through-holes 33 are provided. The sixteen substrate through-holes 33 are provided such that the position and the shape agree and overlap with those of sixteen upper layer through-holes 41a not to allow a part of the reduction electrode body 32 to be exposed, of the upper layer through-holes 41. Of the upper layer through-holes 41, a part of the oxidation electrode body 12 is exposed via the substrate through-hole 33 from the sixteen upper layer through-holes 41a not to allow a part of the reduction electrode body 32 to be exposed. More specifically, hatched portions on the oxidation electrode body 12 in FIG. 2 are brought into contact with the sample solution, and functions as oxidation electrode 12d. In FIG. 2, sixteen oxidation electrodes 12d are provided. Of the oxidation electrode body 12, the part on which the substrate 31 is formed, i.e., a part unhatched without printed designation on the oxidation electrode body 12 in FIG. 2 is not to be in contact with the sample solution. Thus, this part does not function as a oxidation electrode. The oxidation electrode body 12 includes a plurality of branches 12a having a zigzag shape extended in the lengthwise direction while sequentially linking the parts exposed from the upper layer through-hole 41a via the substrate through-hole 33 alternately on the adjacent two columns, and stem 12b that is connected to one end of all branches 12a. In addition, the oxidation electrode body 12 has reduction electrode lead 12c at one end of the stem 12b.

Figure 3:
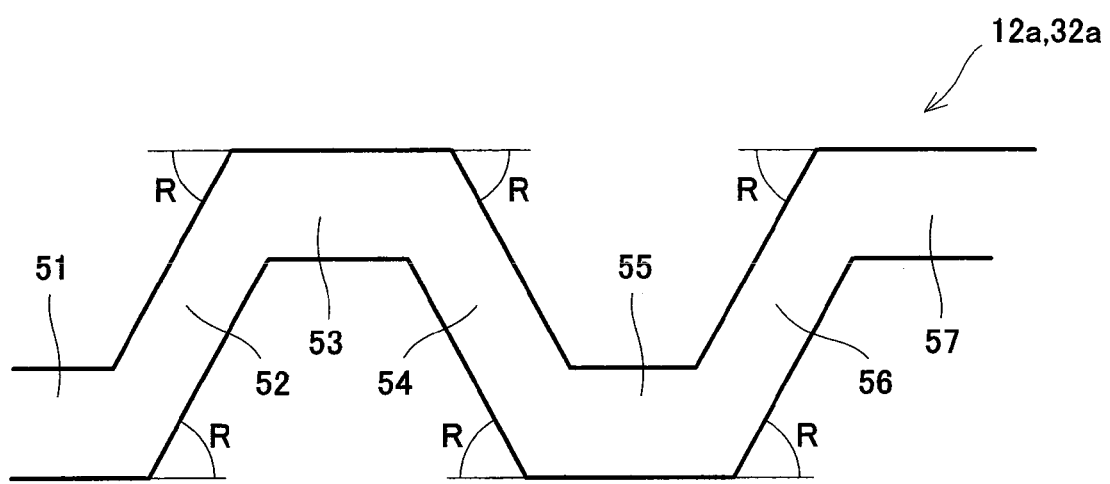
FIG. 3 shows a plan view schematically illustrating a partial shape of the branch of an oxidation electrode body and reduction electrode body.

The shape of the oxidation electrode body 12 and the reduction electrode body 32 in the electrode plate for electrochemical measurements 1 according to this embodiment is explained in more detail with reference to FIG. 3. In this embodiment, the branches 12a and 32a form "zigzag shape", respectively. The term "zigzag shape" means in general, a shape formed by bending a straight line alternately right and left a number of times, or a shape formed by arranging wires having a substantially Z-shape periodically, and this term herein referred to also has the same meaning. FIG. 3 shows a plan view schematically illustrating a partial shape of the branches 12a or 32a of the oxidation electrode body 12 or the reduction electrode body 32. As shown in FIG. 3, the "zigzag shape" in this embodiment is a shape formed with longitudinally directed extended sections 51, 53, 55 and 57 that come out in the longitudinal direction connected to each of the closest longitudinally directed extended sections on the different column, and includes connection portions 52, 54 and 56 provided to exhibit an angle R with respect to the longitudinally directed extended section. The longitudinally directed extended sections 51, 53, 55 and 57 include the oxidation electrode 12d or the reduction electrode 32d, respectively.

Figure 18:
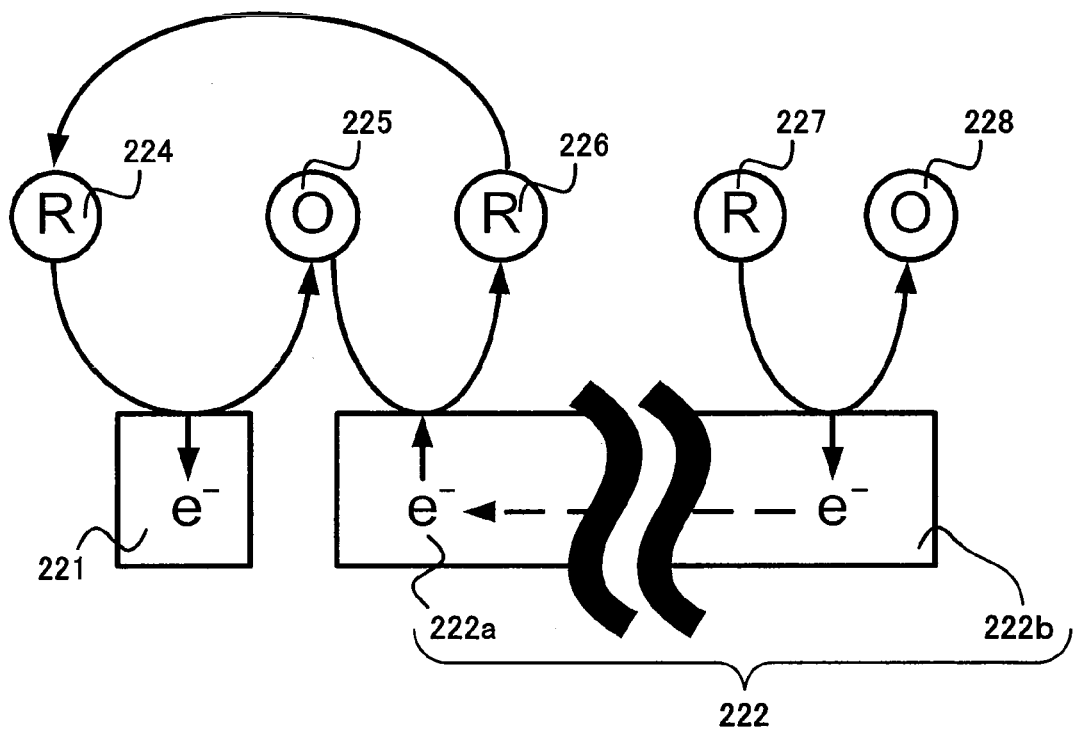
FIG. 18 shows a view schematically illustrating an oxidation-reductive reaction caused on an electrode of a conventional electrode plate for electrochemical measurements.

Again in FIG. 2, the upper layer through-hole 41 and the substrate through-hole 33 are both penetrated in the vertical direction, and have a shape with a substantially constant cross-sectional shape and a constant cross sectional area along the vertical direction. The area of each upper layer through-hole 41 is substantially the same as the area of each substrate through-hole 33. The cross-sectional shape is regular tetragon, and the cross sectional area thereof may be, for example, 1 $\mu m^2$ to 10000 $\mu m^2$. When this area is greater than 10,000 $\mu m^2$, an undesirable reaction as shown on the right side in FIG. 18 occurs, and consequently, problems in elevation of sensitivity may be caused. The lower layer 11, the substrate 31, and the upper layer 40 preferably have a thickness of no greater than 5 μm and no less than 100 μm, respectively. The area of the reduction electrode 32d is the same as the cross sectional area of the upper layer through-hole 41b, while the area of the oxidation electrode 12d is the same as the cross sectional area of the substrate through-hole 33.

The potential can be applied independently to the oxidation electrode body 12 and the reduction electrode body 32, respectively, whereby an electrochemical reaction, more specifically an oxidative reaction and a reductive reaction of the target substance can be proceeded on each electrode. The electric signal generated by the electrochemical reaction on the oxidation electrode 12d is transmitted to through the oxidation electrode body 12, and can be quantitatively determined with a measuring instrument such as a galvanometer via the oxidation electrode lead 12d. Similarly, the electric signal generated by the electrochemical reaction on the reduction electrode 32d is transmitted to through the reduction electrode body 32, and can be quantitatively determined with a measuring instrument such as a galvanometer via the reduction electrode lead 32d.

Each oxidation electrode 12d is adjacent to four reduction electrodes 32d with an even distance between centers in the four directions of up-and-down and right-and-left directions on the plane view. Similarly, each reduction electrode 32d is adjacent to four oxidation electrodes 12d with an even distance between centers in the four directions of up-and-down and right-and-left directions on the plane view. More specifically, each electrode 32d and 12d are adjacent to four electrodes 32d and 12d, respectively, which can act electrochemically through forming pairs, and when an oxidative/reductive substance in a sample solution is quantitatively determined by an electrochemical method using the electrode plate for electrochemical measurements 1 according to this embodiment, the oxidative/reductive substance can be determined with superior accuracy by an efficient redox cycle.

Next, the material of the member constituting the electrode plate for electrochemical measurements 1 according to this embodiment is described in detail. As the lower layer 11, a substrate having insulation properties in its entirety, or on the surface thereof may be used. For example, a silicon substrate having an oxide film on which an $SiO_2$ film is coated as an insulating layer on the surface of a silicon substrate, a quartz glass plate, an aluminum oxide substrate, a substrate formed with a resin material such as a polyethylene terephthalate film, a polyethylene naphthalate film or a polyimide film, or the like can be used.

The oxidation electrode body 12 and the reduction electrode body 32 are formed with a material having electrically conductive properties such as a metal, a metal oxide or a semiconductor. Examples of the material having electrically conductive properties which can be used include metals such as gold, platinum, palladium, silver, chromium, titanium and nickel, semiconductors such as p-type and n-type silicon, p-type and n-type germanium, cadmium sulfide, titanium dioxide, zinc oxide, gallium phosphide, gallium arsenide, indium phosphide, cadmium selenide, cadmium telluride, molybdenum diarsenide, tungsten selenide, copper dioxide, tin oxide, indium oxide and indium tin oxide, as well as electrically conductive carbon such as Kechen black. Gold, platinum or palladium which is stable as an electrode material is preferably used.

The substrate 31 and upper layer 40 can be formed using silicon oxide typified by $SiO_2$ or silicon nitride, with a method such as atmospheric pressure CVD, low pressure CVD, plasma CVD, or sputtering. Alternatively, the substrate 31a can be produced by coating a resin material such as e.g., spin-on glass (Tokyo Ohka Kogyo Co., Ltd.), a silicon resin such as Elastosil (manufactured by Asahi Kasei Wacker Silicones Corporation), polyimide or a derivative thereof such as Kapton® (manufactured by Du Pont-Toray Co., Ltd.), an epoxy resin such as JER (manufactured by Japan Epoxy Resins Co., Ltd.), a thermosetting resin such as Sumicon (manufactured by Sumitomo Bakelite Co., Ltd.), a photoresist agent or a photosensitive resin such as PMER (manufactured by Tokyo Ohka Kogyo Co., Ltd.) or SU8 (manufactured by Kayaku Microchem Co., Ltd.), by spin coating or the like, followed by a procedure including baking, exposure with an electronic beam or an ultraviolet ray, development process and the like in combination. In light of ease of processing in the step for forming pores described later, silicon oxide, silicon nitride, a photoresist material or a photosensitive resin may be preferably used.

Furthermore, when the electrode plate for electrochemical measurements 1 is manufactured, patterning of the conductive material is carried out so as to form the oxidation electrode body 12 on the superior face of the lower layer 11, and the reduction electrode body 32 on the superior face of the substrate 31. For the patterning of the electrode, a combination method involving a film formation procedure such as vapor deposition or sputtering and an etching procedure; a procedure in which a film formation procedure is carried out with a metal mask in combination, a lift off process carried out using a photoresist, screen printing with a mask, a laser ablation process, or direct drawing procedure by an ink jet printing process can be employed.

Formation of the upper layer 40 with a photoresist or photosensitive resin material carried out after lamination is orderly carried out on the lower layer 11 to form the reduction electrode body 32 is now explained. A precursor material of the photosensitive resin for use in forming the upper layer 40 is applied on the substrate 31 having the reduction electrode body 32 formed thereon, and then a baking step is carried out. An image mask having a pattern in which a plurality of regular tetragonal pores having an equal area are arranged in the lateral direction and the lengthwise direction with an even distance between centers is overlaid thereon, and the mask pattern is exposed with an electronic beam, an ultraviolet ray or the like, and developed to transfer the pattern to the photoresist or the photosensitive resin material on the substrate, followed by subjecting to development and baking line to obtain upper layer 40 having the upper layer through-holes 41. By etching the substrate 31 using the upper layer 40 as a mask, substrate through-holes 33 are formed. Alternatively, the substrate through-holes 33 may be formed prior to the step of laminating the upper layer 40.

According to the method for production described above, the upper layer through-holes 41 and the substrate through-holes 33 having the same cross-sectional shape and the same cross sectional area can be readily formed, whereby coordination to give even concentrations of the reaction products yielded from the oxidation electrode 12d and the reduction electrode 32d, respectively cam be facilitated. In addition, by coordinating to give even distance between centers of the counter electrodes equal rate of the redox cycle reaction that proceeds between each of the counter electrodes can be achieved. These actions enable the steady state to be quickly attained. As a result, quantitative determination of the target substance included in the sample solution can be perfected with superior accuracy.

In the electrode plate for electrochemical measurements 1 according to this embodiment, the upper layer through-hole 41 and the substrate through-hole 33 serve as a paths of the sample solution; therefore, the inner walls of the upper layer through-hole 41 and the substrate through-hole 33 are desirably hydrophilic when the sample solution is an aqueous solution. Thus, it is desired to select as the upper layer 40 and the substrate 31, a substrate having a hydrophilic surface such as a silicon substrate or a glass substrate, or a substrate constructed with a hydrophilic polyester material such as a polyethylene terephthalate or polyethylene naphthalate substrate. When a hydrophobic substrate is used, it is desired to subject the inner wall of the upper layer through-hole 41 or the substrate through-hole 33 to a hydrophilizing treatment with ethanol, isopropyl alcohol or the like.

Explanation of Apparatus for Electrochemical Measurements

Figure 4:
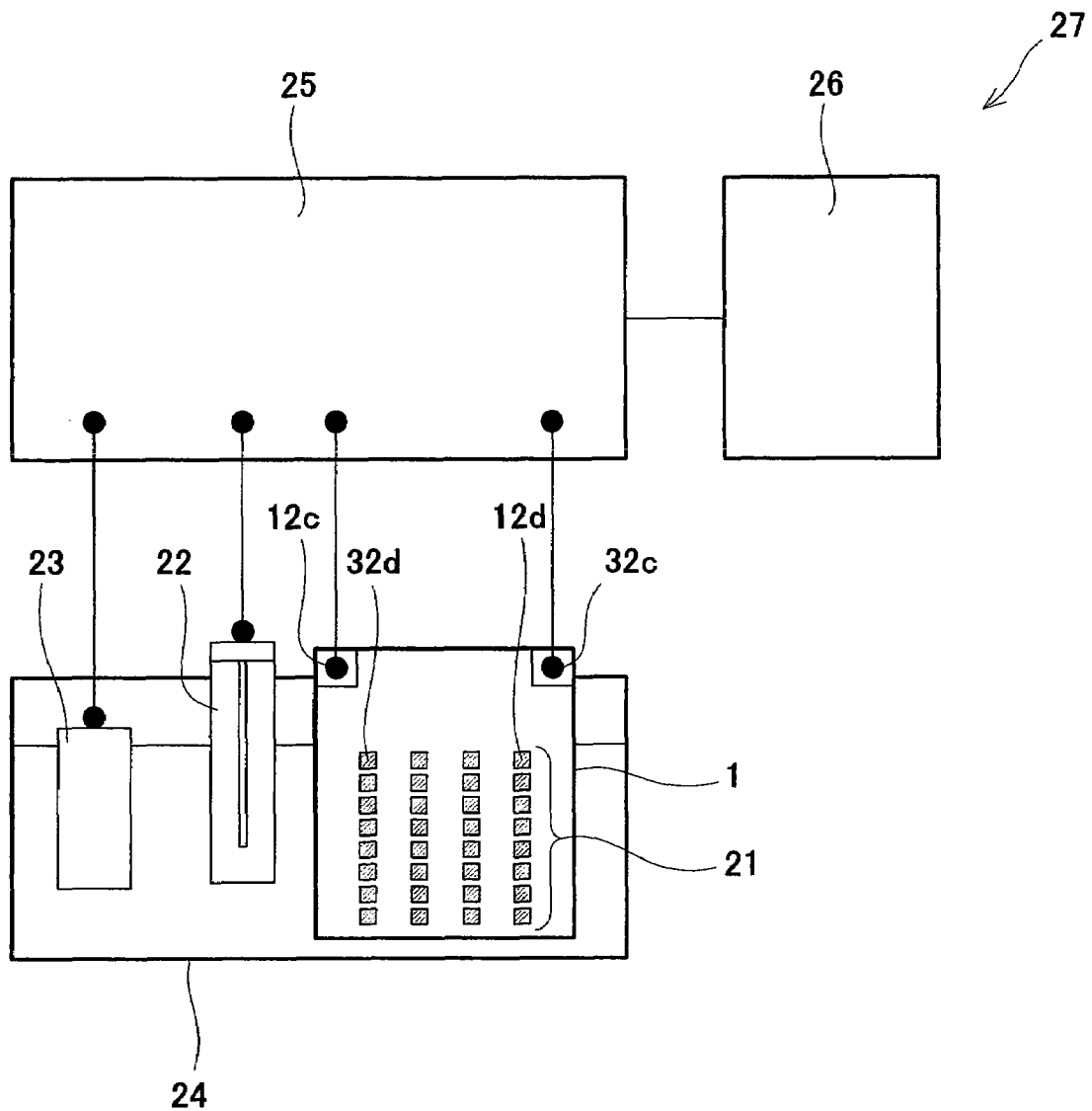
FIG. 4 shows a schematic view illustrating an apparatus for electrochemical measurements including an electrode plate for electrochemical measurements according to the first embodiment.

FIG. 4 shows an apparatus for electrochemical measurements having an electrode plate for electrochemical measurements (hereinafter, may be merely referred to as "measurement apparatus") according to the first embodiment.

As shown in FIG. 4, the electrode plate for electrochemical measurements 1, reference electrode 22, and auxiliary electrode 23 are immersed in a sample solution filled in sample vessel 24 in measurement apparatus 27. Accordingly, these electrodes are brought into contact with the sample solution. In addition, a plural number of oxidation electrodes 12d and reduction electrodes 32d are formed alternately in the lateral direction and the lengthwise direction on the surface of the electrode plate for electrochemical measurements 1, thereby forming electrode assembly 21. The reference electrode 22 is an electrode that serves in representing a standard of the potential applied to the electrode plate for electrochemical measurements 1. The potential shown by the reference electrode 22 in the sample solution is defined as zero, and the potentials are applied to the oxidation electrode 12d and the reduction electrode 32d, respectively.

The auxiliary electrode 23 is an electrode for compensating the electric current so as to conform to Ampere's law in the measurement apparatus 27. The control unit 25 is electrically connected to the electrode plate for electrochemical measurements 1 via the oxidation electrode lead 12c and reduction electrode lead 32c, and also, electrically connected to the reference electrode 22 and the auxiliary electrode 23. The electric current response that is output from the control unit 25 is recorded by recorder 26.

Explanation of Electrochemical Measuring Method

Next, a method for quantitatively determining the electronic mediator included in a sample solution is explained.

According to a process such as cyclic voltammetry, the potential to allow the oxidative reaction to proceed, and the potential to allow the reductive reaction to proceed in the electronic mediator are determined beforehand, and used for the potential value of the oxidation electrode and the potential value of the reduction electrode described later. The standard of the potential is an equilibrium potential represented by the reference electrode 22 in the sample solution. In other words, the potentials applied to the oxidation electrode 12d and the reduction electrode 32d, respectively, are a relative potential defined for the reference electrode 22 as 0 V.

After the potentials of the oxidation electrode 12d and the reduction electrode 32d are entered into the control unit 25, the measurement is started. Although explained in detail in Examples described later, specifically, positive voltage is slowly applied from 0 V to the oxidation electrode 12d. In Examples described later, the voltage applied to the oxidation electrode 12d is altered slowly from 0 V to +0.7 V. Such application is referred to as "sweeping". That is, the term "sweeping" used herein means to alter the potential continuously. In contrast, the term "applying" used herein means to alter a predetermined potential rapidly.

In this procedure, it is preferred to keep applying the same potential (0 V, in many cases) to the reduction electrode as that of the reference electrode. The speed of applying the voltage (hereinafter, may be also referred to as "sweeping speed") to the oxidation electrode 12d is generally 5 mV/sec or greater and 500 mV/sec or less. In Examples described later, the speed is 100 mV/sec.

In the foregoing description, a positive potential is swept to the oxidation electrode 12d, while a negative potential is applied to the reduction electrode 32d. However, a positive potential may be applied to the oxidation electrode 12d, while a negative potential may be swept to the reduction electrode 32d.

The electric current obtained by an oxidative reaction on the oxidation electrode 12d is detected by control unit 25 via the oxidation electrode lead 12c. Similarly, the electric current obtained by a reductive reaction on the reduction electrode 32d is detected by control unit 25 via the reduction electrode lead 32c. Thus detected electric current is output to the recorder 26, and thus the substance to be detected in the sample solution can be quantitatively determined by comparing the recorded oxidation current with a result of measurement (calibration curve described later) of the oxidation current values of a standard sample.

It is also possible to quantitatively determine the substance to be detected in the sample solution by comparing the reduction electric current value recorded on the recorder 26 with a result of measurement of the reduction electric current of a standard sample. For this purpose, it is desirable to produce a calibration curve of the standard sample beforehand using a detection device of this Embodiment.

A method for quantitatively determining the substance to be detected in a sample solution using a calibration curve, i.e., a method of calculating the concentration of the substance to be detected in the sample solution is explained below.

A standard sample is first provided. This standard sample contains a reduced electronic mediator (herein, assumed as potassium ferrocyanide) having a known concentration. Using such a standard sample having a known concentration as a sample solution having a known concentration, relationship between the concentration of the reduced electronic mediator, and the kinetic current value measured with the apparatus for electrochemical measurements is indicated on a graph by means of the apparatus for electrochemical measurements as illustrated in FIG. 4. One example of this graph is shown in FIG. 5.

Figure 5:
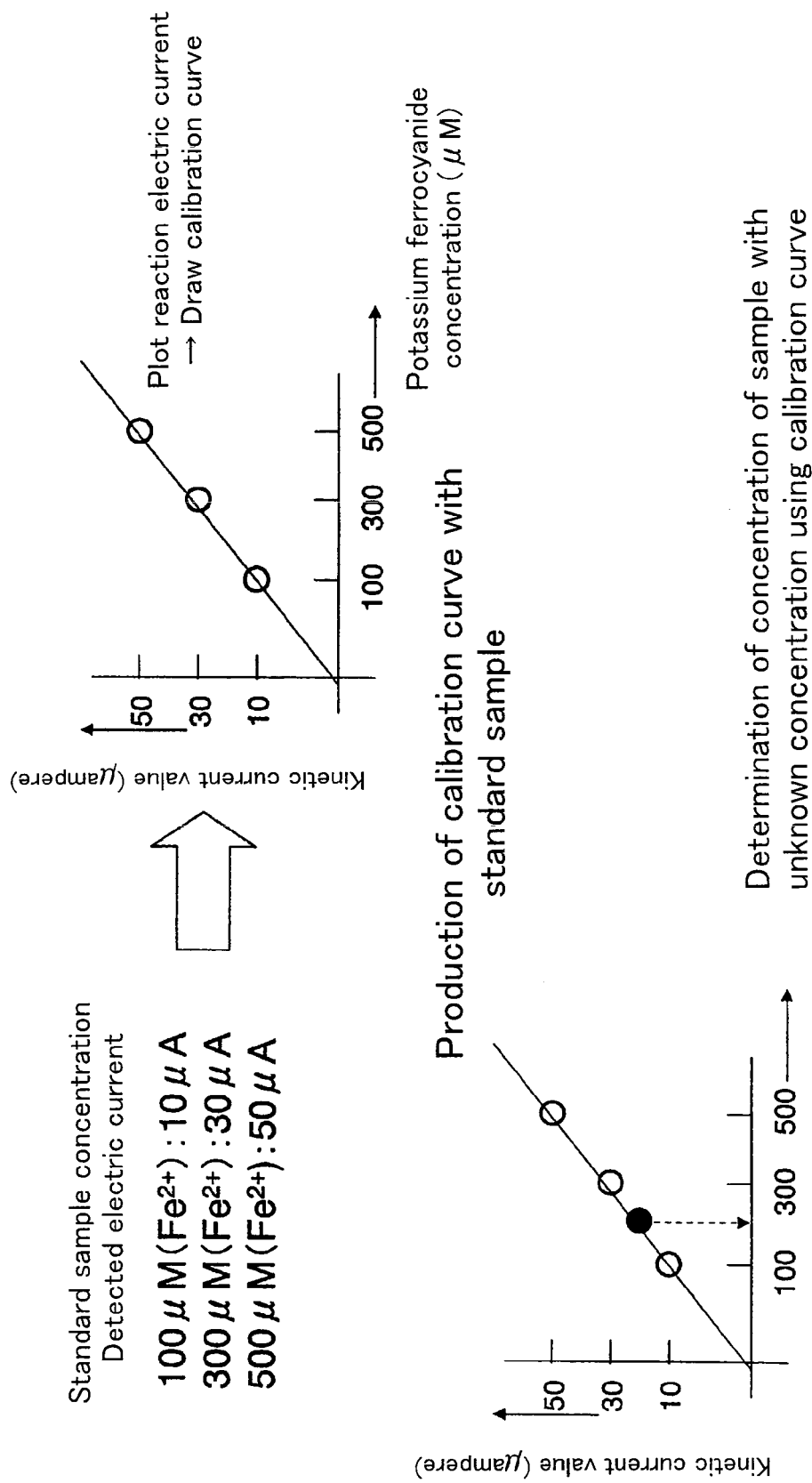
FIG. 5 shows a view illustrating one example of a process for producing a calibration curve.

As illustrated on the graph shown in FIG. 5, kinetic current values are plotted against the potassium ferrocyanide concentration to produce a calibration curve. Thus, when a kinetic current value of 20 μA is derived on a sample having an unknown concentration, the potassium ferrocyanide concentration of 200 μM is proven from the calibration curve produced, as shown in the bottom graph in FIG. 5. Accordingly, quantitative determination of the potassium ferrocyanide concentration on a sample having an unknown concentration using the calibration curve is enabled.

As shown in FIG. 4, it is assumed herein that: the kinetic current value was 10 μA when the concentration of the reduced electronic mediator is 100 μM; kinetic current value is 30 μA when the concentration of the reduced electronic mediator is 300 μM; and the kinetic current value is 50 μA when the concentration of the reduced electronic mediator is 500 μM. These data are plotted on a graph to draw a calibration curve. Accordingly, a calibration curve is obtained from a standard sample having a known concentration.

Next, using a sample solution the concentration of which is unknown, a kinetic current value is obtained with an apparatus for electrochemical measurements as shown in FIG. 4. When the kinetic current value obtained in this procedure is 20 μA, the concentration of the reduced electronic mediator included in the sample solution can be revealed from the calibration curve. The amount of the target substance which is/was included in the sample solution is calculated based on this concentration of the reduced electronic mediator.

It would not be necessary to mention that production of the calibration curve, calculation of the amount of the target substance, and the like may be all carried out on a computer, in effect.

Explanation of Reference Electrode, and Auxiliary Electrode

It is also possible carry out the measurement using one counter electrode in place of the two electrodes, i.e., the reference electrode 22 and the auxiliary electrode 23. However, it is preferred to provide the reference electrode 22 and the auxiliary electrode 23 independently because the electrode reaction proceeds on the surface while the electric current flows to the counter electrode or the reference electrode to be a standard of the potential, and the potential employed as a standard of the detection device of this Embodiment varies when alteration of the concentration of the electronic mediator is enhanced as the reaction proceeds, whereby accurate measurement cannot be executed.

Therefore, it is desirable to preset the input impedance as large as possible so as not to prevent the electric current from flowing to the reference electrode 22. It is desired that the impedance value is equal to or greater than $10^6$ ohm. A silver-silver chloride electrode, a saturated calomel electrode or the like can be used for the reference electrode 22.

It is desired that the auxiliary electrode 23 has a large surface area. Preferred surface area of the auxiliary electrode 23 is ten times larger than that of the assembly 21 of the electrode because when sufficient electric current cannot be flowed due to too small electrode surface area of the auxiliary electrode 23, the electric current obtained with the electrode plate for electrochemical measurements 1 does not flow enough to the control unit 25, whereby an accurate electric current value is not yielded, and additionally, the potential of the auxiliary electrode 23 greatly varies for allowing the electric current to flow, thereby leading to undesirable reactions such as electrolysis of water may be proceeded.

It is desired that a noble metal electrode that is less likely to cause an oxidation-reduction reaction of the electrode per se or a corrosion reaction is used as the auxiliary electrode 23. For example, platinum electrodes are preferred which are produced by depositing platinum black on a platinum wire to provide a great electrode area.

Figure 6:
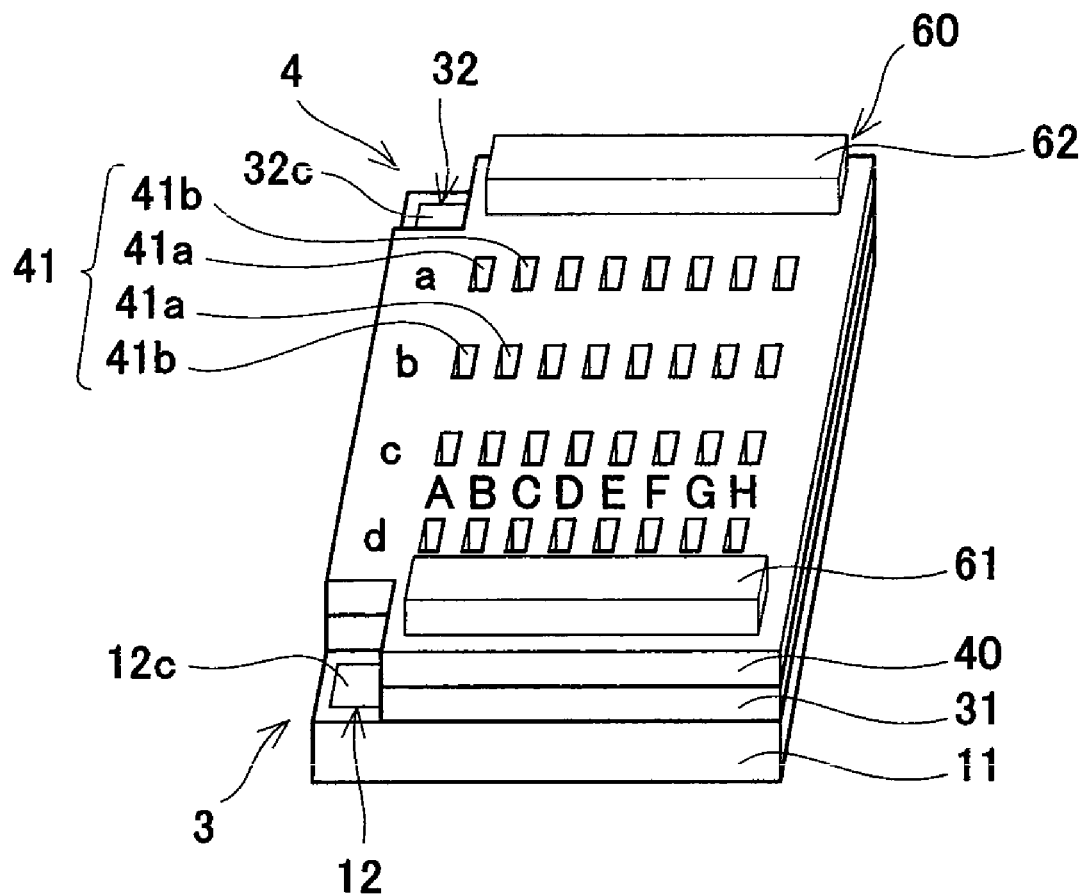
FIG. 6 shows a perspective view schematically illustrating an electrode plate in which a reference electrode and an auxiliary electrode are formed on the electrode plate for electrochemical measurements according to the first embodiment.

FIG. 6 shows an electrode plate that constructs a measurement apparatus distinct from the apparatus for electrochemical measurements shown in FIG. 4. In the electrode plate for electrochemical measurements 60 shown in FIG. 4, reference electrode 61 and auxiliary electrode 62 are formed integrally with the electrode plate for electrochemical measurements 1 according to the first embodiment. The reference electrode 61 and the auxiliary electrode 62 are formed on the upper layer 40. More specifically, a resist is applied on the surface of the electrode plate for electrochemical measurements 1 according to the first embodiment, and after an image mask having a pattern of the reference electrode and the counter electrode is overlaid thereon, the pattern is exposed with an ultraviolet ray or an electronic beam, followed by development to transfer the pattern to the resist on the substrate. Thereafter, the electrode layer is formed by a procedure such as sputtering, vapor deposition, CVD, screen printing or ink printing, followed by production of the reference electrode 61 and the auxiliary electrode 62 by a lift off process for detaching the resist. Accordingly, the electrode plate 60 in which the oxidation electrode 12d and reduction electrode 32d as a working electrode, the reference electrode 61, and the auxiliary electrode 62 are integrated can be obtained. In this case, for producing the reference electrode 61, one electrode other than the working electrode is selected, and a metal or an organic oxidation-reduction polymer to be an indicator is provided thereon by a plating, electrolytic polymerization, or printing process. In addition, as the indicator for providing on the reference electrode 61, silver, silver chloride, polyvinylferrocene and the like may be exemplified.

In the case of the electrode plate for electrochemical measurements 60, three electrodes, i.e., working electrode, reference electrode and counter electrode are formed within a plate-like single electrode plate for electrochemical measurements 60, therefore, the apparatus for electrochemical measurements constructed using the same is suited for the measurement of small samples and in trace concentration regions, and Particularly suitable for analyses of biological samples.

Second Embodiment

Figure 7:
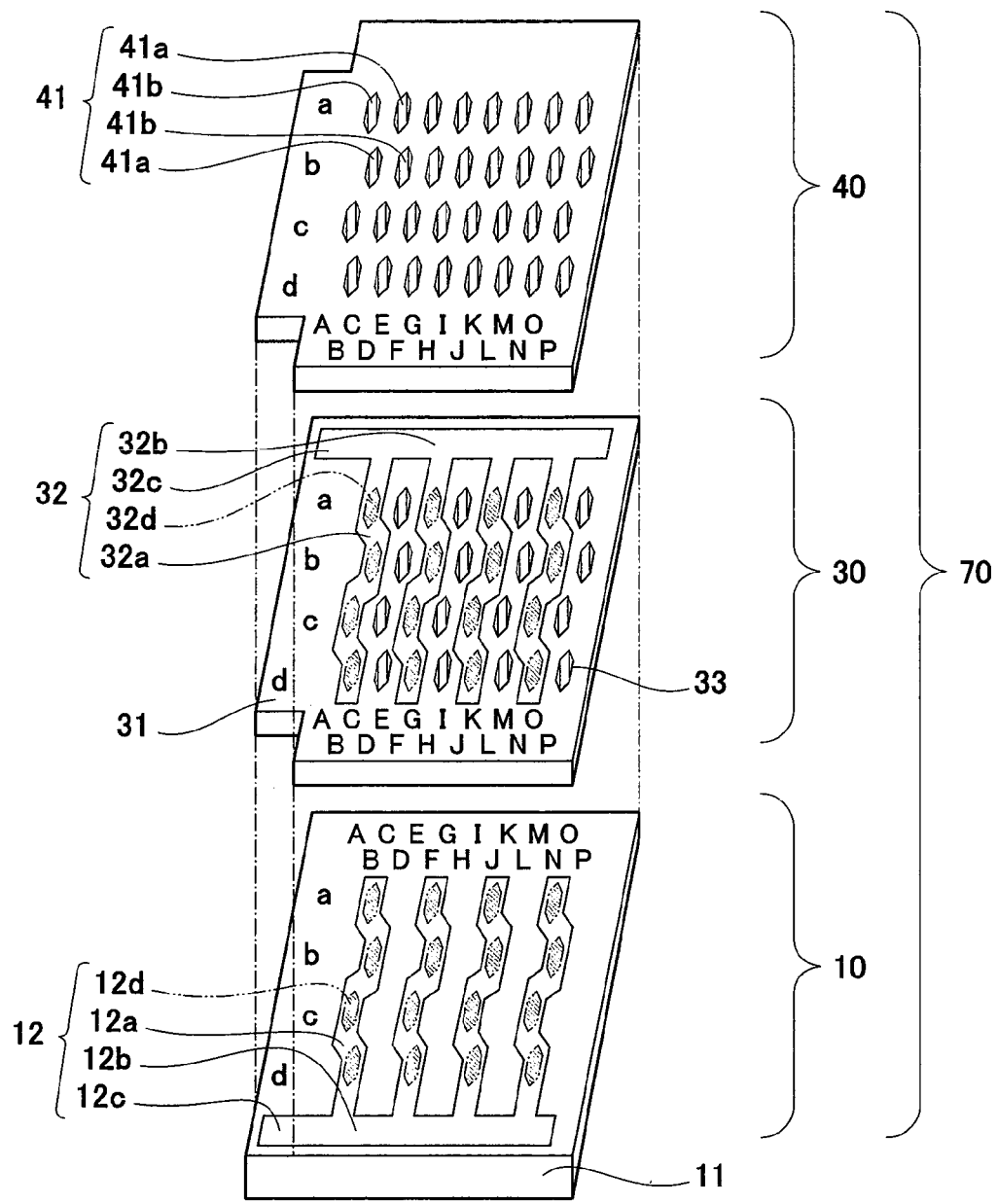
FIG. 7 shows an exploded perspective view schematically illustrating an electrode plate for electrochemical measurements according to the second embodiment.

FIG. 7 shows an exploded perspective view schematically illustrating electrode plate for electrochemical measurements 70 according to the second embodiment. The electrode plate for electrochemical measurements 70 according to this embodiment is different from the electrode plate for electrochemical measurements 1 according to the first embodiment in that: the shape of the through-holes formed in the upper layer 40 and the substrate 31 is not regular tetragonal but regular hexagonal; the through-holes in the upper layer 40 and the substrate 31 are arranged in a different manner; and the shape of the branch 12a of the oxidation electrode body 12 is different from that of the branch 32a of the reduction electrode body 32. In the following, only such differences from the electrode plate for electrochemical measurements 1 according to the first embodiment will be explained.

Figure 8:
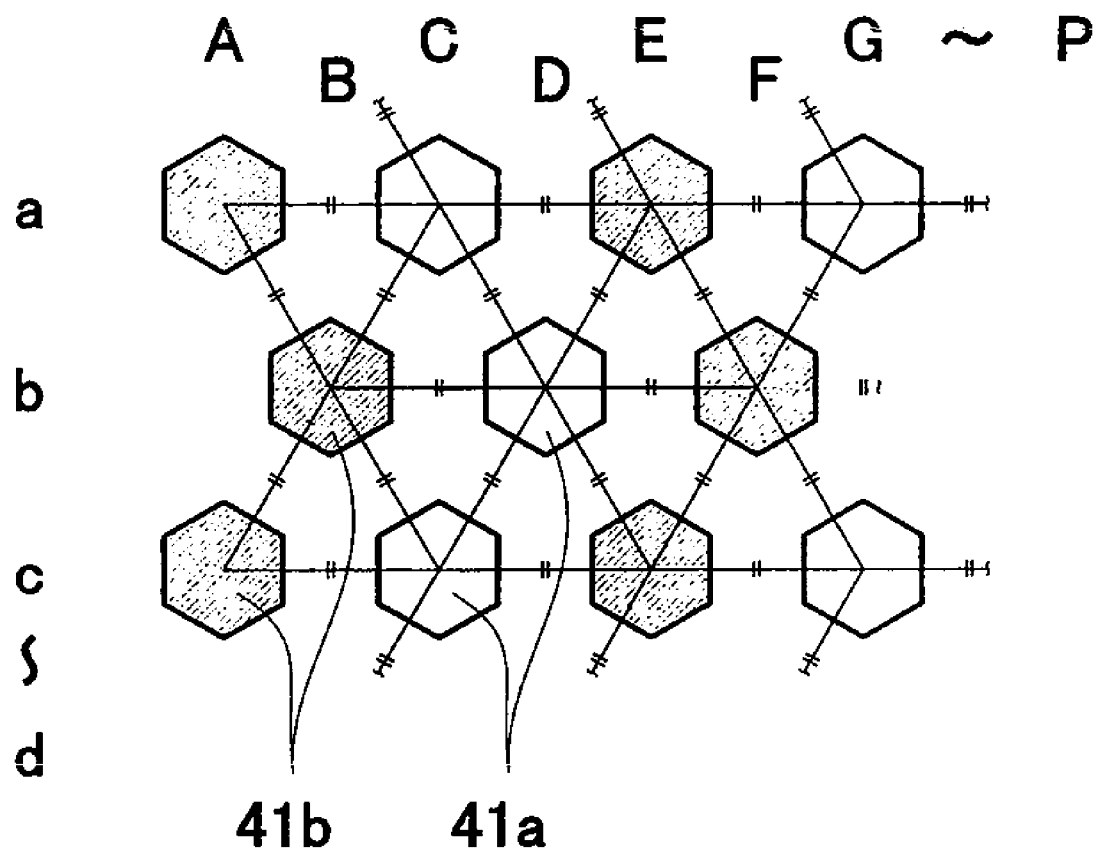
FIG. 8 shows a top view illustrating a part of arrangement of the upper layer through-holes in the electrode plate for electrochemical measurements shown in FIG. 7.

In the electrode plate for electrochemical measurements 70 according to this embodiment, the upper layer through-hole 41, and the substrate through-hole 33 have a cross-sectional shape of regular hexagon. The arrangement of a plurality of upper layer through-holes 41 in the upper layer 40 is first explained. Positions where the upper layer through-holes 41 are arranged along the lateral direction are designated with reference signs of A to P, while those along the lengthwise direction are designated with reference signs of a to d. The upper layer through-holes 41 are formed at positions a and c along the lengthwise direction, and positions (A, C, E, . . . , K, M, O) along the lateral direction. Similarly, at the positions c and d along the lengthwise direction, the upper layer through-holes 41 are formed at (B, D, F, . . . , L, N, P). FIG. 8 shows a top view illustrating a part of arrangement of the upper layer through-holes 41 in the upper layer 40. In FIG. 8, for the sake of expedience, only the upper layer through-holes 41*b* to allow the reduction electrodes 32*d* to be exposed are hatched, which are distinguished from the upper layer through-holes 41*a* to allow the oxidation electrode 12*d* to be exposed. Moreover, straight lines are drawn in between the upper layer through-holes 41 positioned closest to some upper layer through-holes 41, whereby confirmation of the positional relationship with the closest upper layer through-holes 41 can be facilitated. On the upper layer 40, the upper layer through-holes 41*b* and the upper layer through-holes 41*a* are arranged along the orientation of each line (the positions along the lengthwise direction being a to d) alternately so as to give the same distance between centers. Then, the identical arrangement is repeated on every other line. One upper layer through-hole 41*a* is arranged at regular intervals with four upper layer through-holes 41*b*. Similarly, one upper layer through-hole 41*b* is arranged at regular intervals with four upper layer through-holes 41*a*. For example, when one upper layer through-hole 41*a* (D, b) is taken as an example, the construction includes four upper layer through-holes 41*b* (E, a), (B, b), (E, c), (F, b) formed therearound so as to be adjacent with an even distance between centers.

In the substrate 31, substrate through-holes 33 are formed so as to correspond to the upper layer through-holes 41*a*. In addition, the reduction electrode body 32 is formed so as not to be in contact with the substrate through-hole 33, and to include regions corresponding to the upper layer through-holes 41*b*. More specifically, in connection with the branch 32*a* of the reduction electrode body 32, adjacent two columns (A and B, C and D, E and F, . . . , M and N, and O and P) in which the upper layer through-holes 41*b* are formed are taken as a set, which are extended from one to another and form a zigzag shape such that regions corresponding to upper layer through-holes 41*b* in the identical set are included, and that these are alternately linked. Furthermore, one end of all the branches 32*a* are connected to the stem 32*b*, whereby the electric current yielded at the branch 32*a* is put together.

Additionally, the oxidation electrode body 12 has a shape similarly to the shape of the reduction electrode body 32, with a plurality of branches 12*a* and stem 12*b*.

The upper layer through-holes 41 and the substrate through-holes 33 are all penetrated in the vertical direction, and have a shape with a substantially constant cross-sectional shape and a constant cross sectional area in the vertical direction. The cross-sectional shape is regular hexagonal, while the cross sectional area is preferably 1 µm² to 10,000 µm².

Since the electrode plate for electrochemical measurements 70 according to this embodiment has a construction as described above, similar effects to those of the electrode plate for electrochemical measurements 1 according to the first embodiment can be achieved. Thus, when the concentration of electronic mediators in a sample solution is quantitatively determined by an electrochemical method using the electrode plate for electrochemical measurements 70 according to this embodiment, the concentration of electronic mediators can be determined with superior accuracy by an efficient redox cycle.

Third Embodiment

Figure 9:
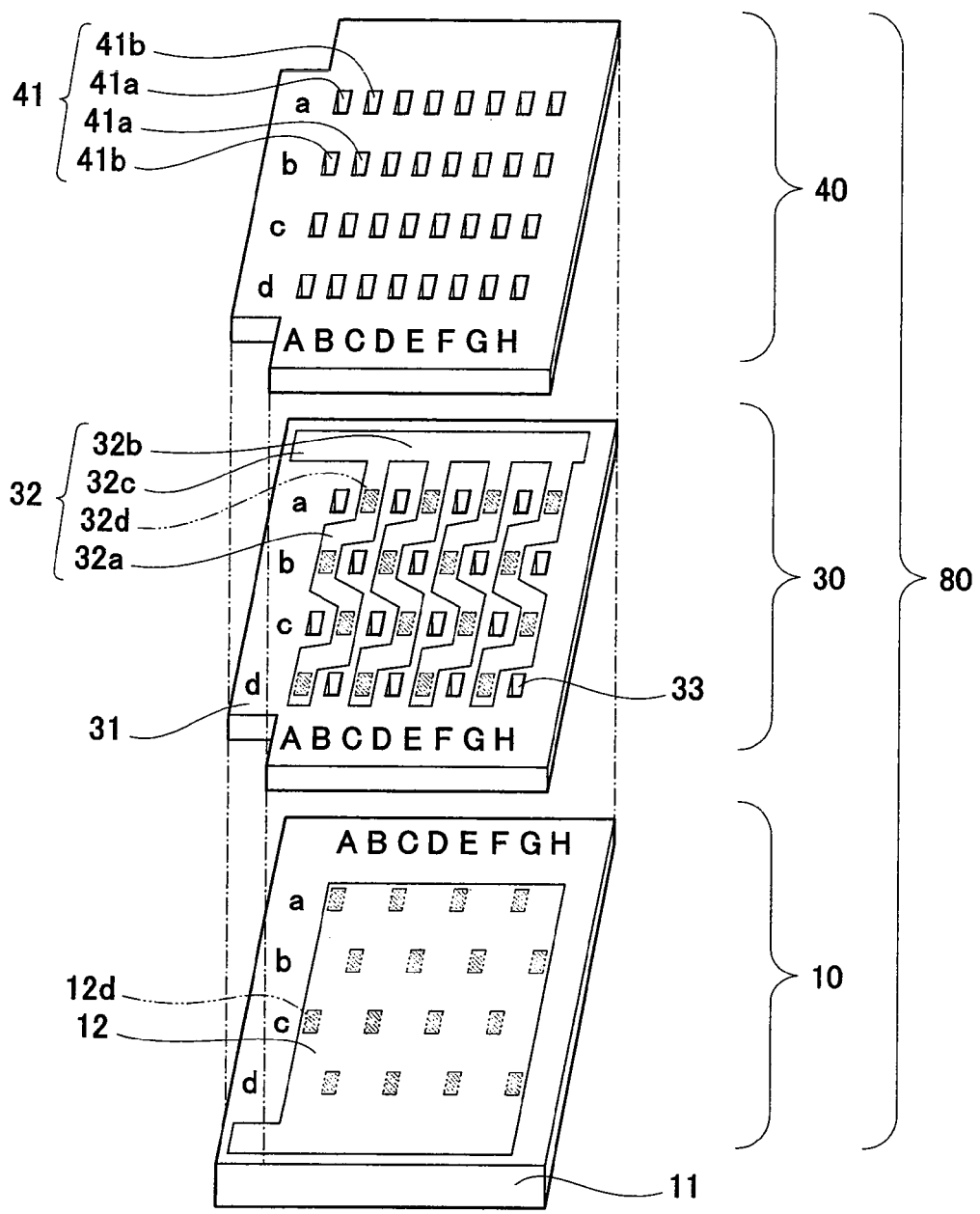
FIG. 9 shows an exploded perspective view schematically illustrating the electrode plate for electrochemical measurements according to the third embodiment.

FIG. 9 shows an exploded perspective view schematically illustrating electrode plate for electrochemical measurements 80 according to the third embodiment. The electrode plate for electrochemical measurements 80 according to this embodiment is different from the electrode plate for electrochemical measurements 1 according to the first embodiment in the shape of the oxidation electrode body 12. In this embodiment, the oxidation electrode body 12 does not have a branch, and is made of a metal plate that involves the regions corresponding to the substrate through-holes 33 in their entirety. In this embodiment, need of an exquisite patterning step of the oxidation electrode body 12 can be avoided.

Fourth Embodiment

Figure 10:
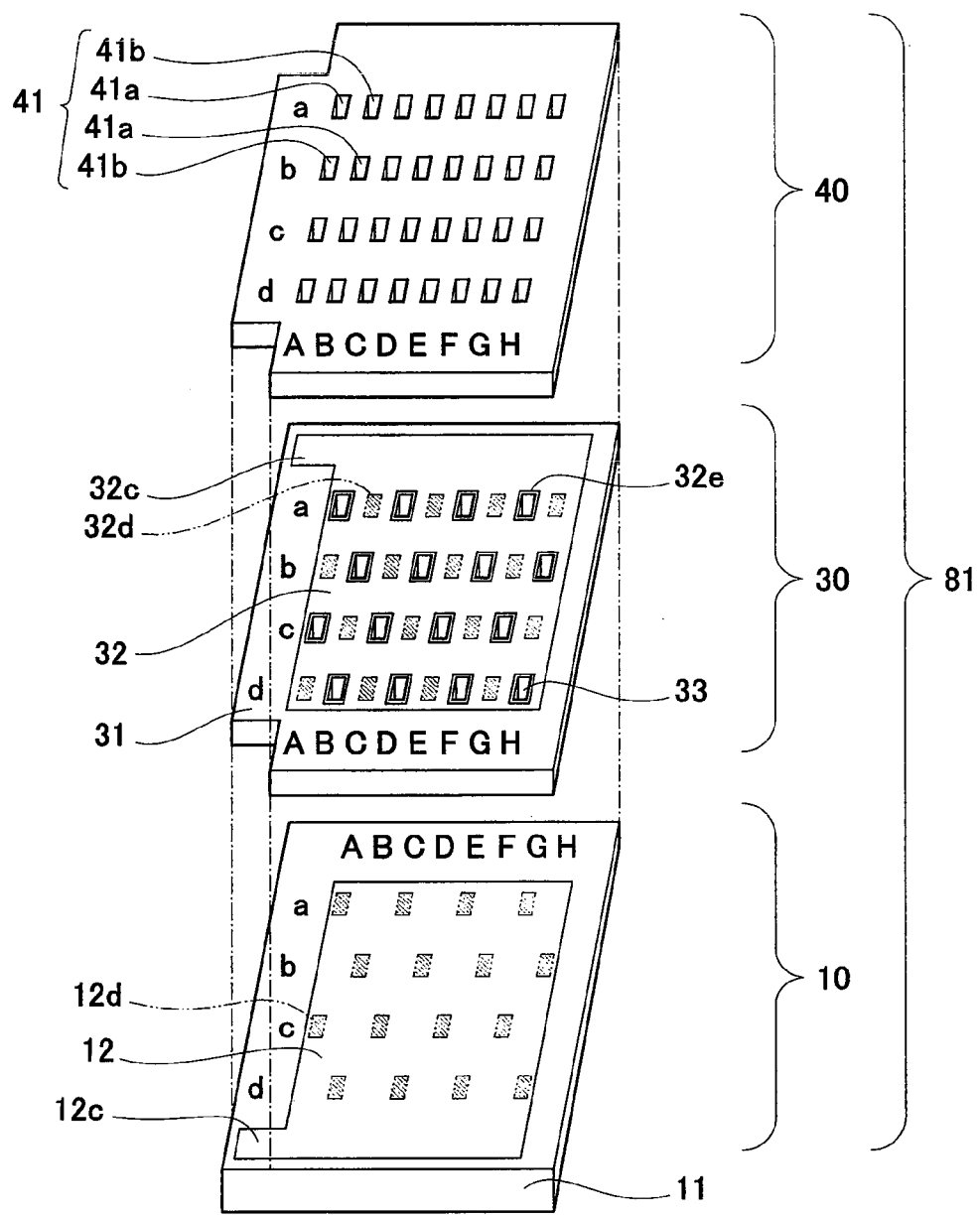
FIG. 10 shows an exploded perspective view schematically illustrating the electrode plate for electrochemical measurements according to the fourth embodiment.

FIG. 10 shows an exploded perspective view schematically illustrating electrode plate for electrochemical measurements 81 according to the fourth embodiment. The electrode plate for electrochemical measurements 81 according to this embodiment is different from the electrode plate for electrochemical measurements 1 according to the first embodiment in the shapes of the oxidation electrode body 12 and the reduction electrode body 32. The oxidation electrode body 12 in this embodiment does not have a branch, and is made of a metal plate that involves the regions corresponding to the substrate through-holes 33 in their entirety. The reduction electrode body 32 does not similarly have a branch, and is made of a metal plate that has a plurality of cut-parts 32*e* formed by cutting off to be slightly larger than regions where the substrate through-holes 33 are formed.

Fifth Embodiment

Figure 11:
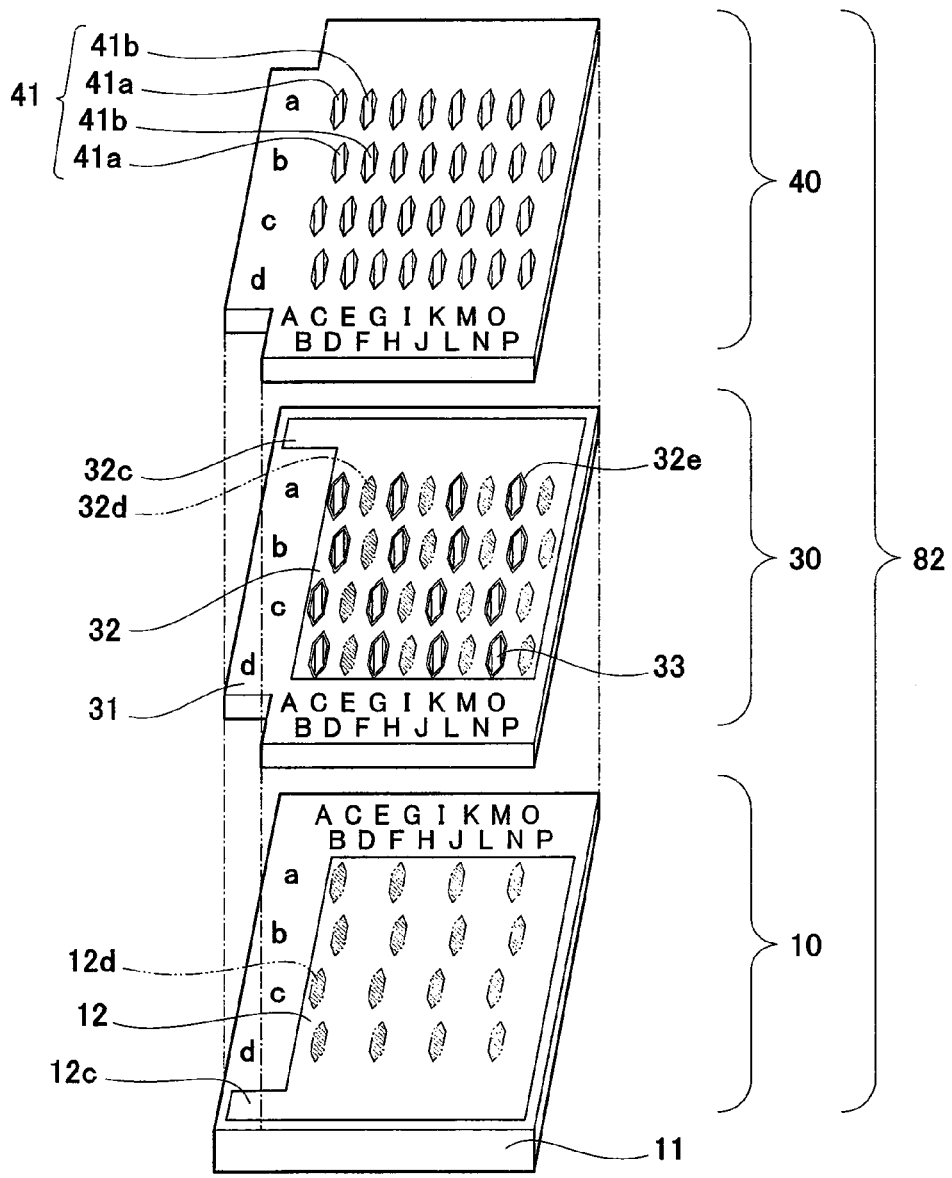
FIG. 11 shows an exploded perspective view schematically illustrating the electrode plate for electrochemical measurements according to the fifth embodiment.

FIG. 11 shows an exploded perspective view schematically illustrating electrode plate for electrochemical measurements 82 according to the fifth embodiment. The electrode plate for electrochemical measurements 82 according to this embodiment is different from the electrode plate for electrochemical measurements 70 according to the second embodiment shown in FIG. 7 in the shapes of the oxidation electrode body 12 and the reduction electrode body 32. The oxidation electrode body 12 does not have a branch, and is made of a metal plate that involves the regions corresponding to the substrate through-holes 33 in their entirety. Moreover, the reduction electrode body 32 does not have a branch, and is made of a metal plate that has a plurality of cut-parts 32*e* formed by cutting off to be slightly larger than regions where the substrate through-holes 33 are formed.

Sixth Embodiment

Figure 12:
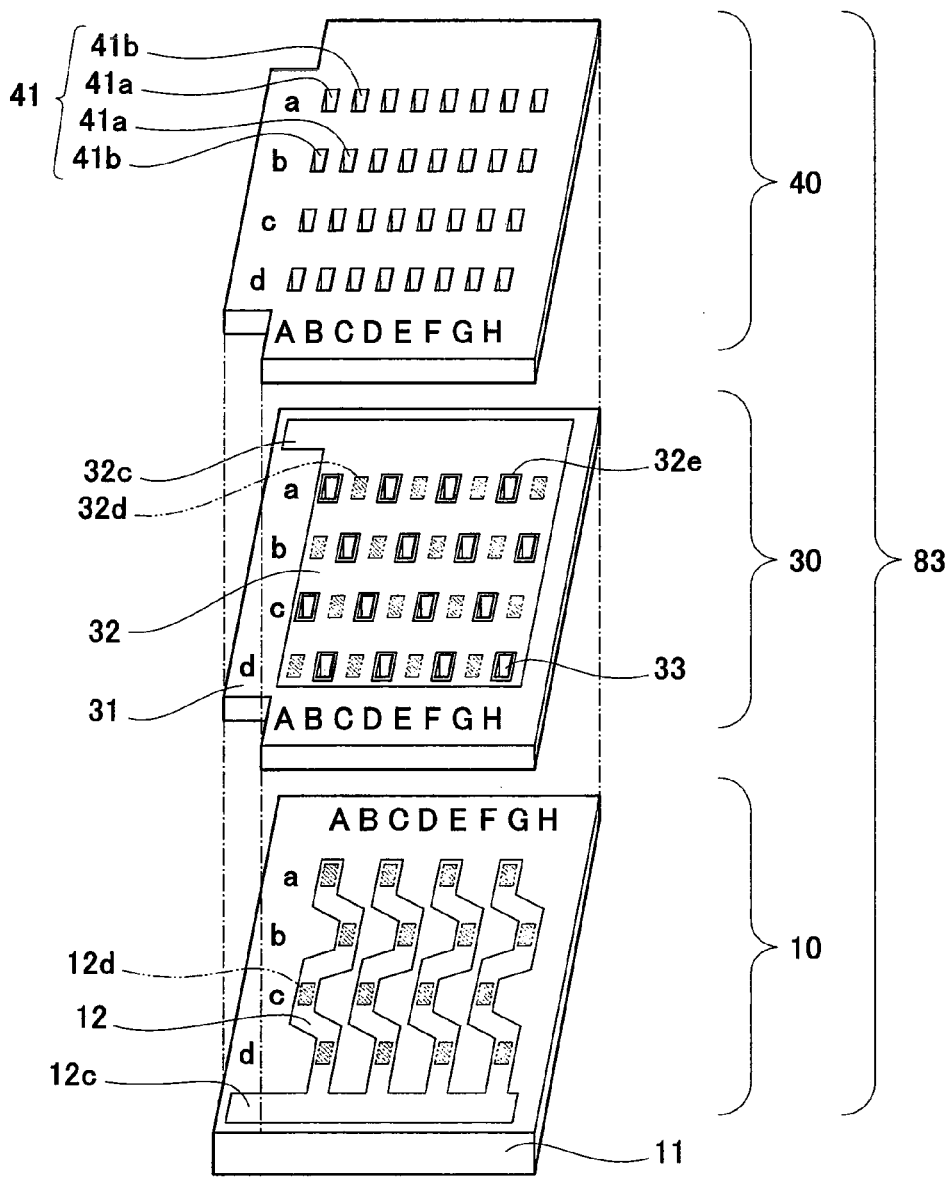
FIG. 12 shows an exploded perspective view schematically illustrating the electrode plate for electrochemical measurements according to the sixth embodiment.

FIG. 12 shows an exploded perspective view schematically illustrating electrode plate for electrochemical measurements 83 according to the sixth embodiment. The electrode plate for electrochemical measurements 83 according to this embodiment is different from the electrode plate for electrochemical measurements 1 according to the first embodiment in the shape of the reduction electrode body 32. The reduction electrode body 32 in this embodiment does not have a branch, and is made of a metal plate that has a plurality of cut-parts 32*e* formed by cutting off to be slightly larger than regions where the substrate through-holes 33 are formed.

Seventh Embodiment

Figure 13:
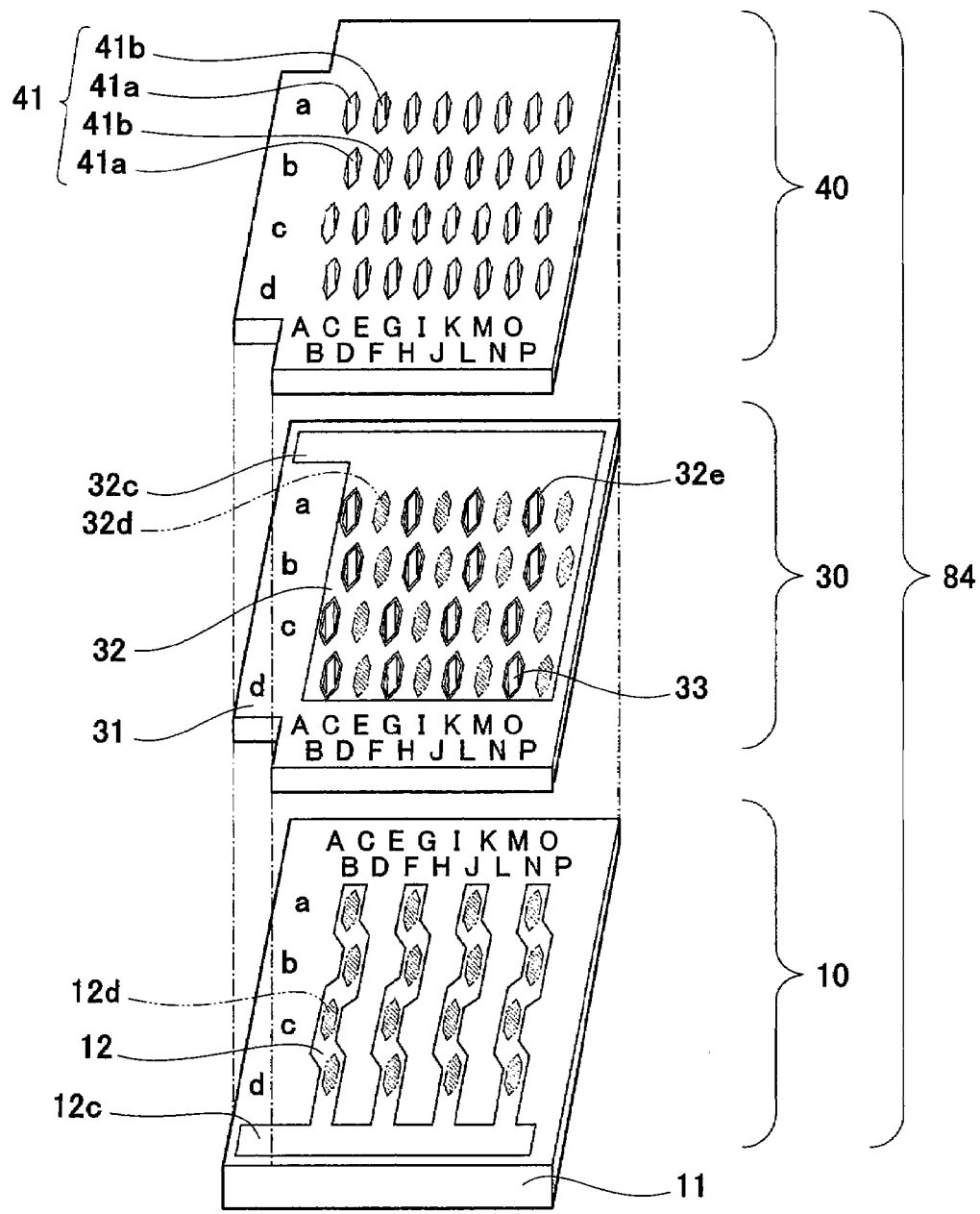
FIG. 13 shows an exploded perspective view schematically illustrating the electrode plate for electrochemical measurements according to the seventh embodiment.

FIG. 13 shows an exploded perspective view schematically illustrating electrode plate for electrochemical measurements 84 according to the seventh embodiment. The electrode plate for electrochemical measurements 84 according to this embodiment is different from the electrode plate for electrochemical measurements 70 according to the second embodiment shown in FIG. 7 in the shape of the reduction electrode body 32. The reduction electrode body 32 in this embodiment does not have a branch, and is made of a metal plate that has a plurality of cut-parts 32e formed by cutting off to be slightly larger than regions where the substrate through-holes 33 are formed.

In the embodiments described in the foregoing, the cases in which two working electrodes (oxidation electrode, reduction electrode) are formed as the working electrode are demonstrated, but the present invention is not limited thereto, and constructions in which other electrode is additionally formed, and two or more working electrodes are used arbitrarily in combination are also acceptable. The redox cycle reaction is allowed to proceed between two electrodes using the electrode plate for electrochemical measurements having such a construction, while other electrode may be used to allow a reaction for eliminating interfering substances included in the sample solution to proceed. The electrode plate for electrochemical measurements having such a construction can exclude electric current response of interfering substances, and is thus suited for analyses of sample solutions including several types of components. Therefore, it is suitable for analyses of biological samples constituted with a variety of components.

Using an electrode plate for electrochemical measurements having a similar construction to those in the embodiments described above, chemical reactions reverse from those in the foregoings (oxidative reaction and reductive reaction) may be allowed to proceed in the oxidation electrode body 12 and the reduction electrode body 32. More specifically, the electrode body 12 may be employed as the reduction electrode body, whereas the electrode body 32 may be employed as the oxidation electrode body.

Also in the embodiments described above, only the cases in which the shape of the upper layer through-hole 41 and the substrate through-hole 33 is a regular tetragon (first, third, and fourth Embodiments), and a regular hexagon (second, and fifth Embodiments) are demonstrated, but the present invention is not limited thereto, and provided that the cross-sectional shape of each pore is identical, rectangle, or other polygon, as well as circle is acceptable. However it should be noted that regular tetragaon or regular hexagon is preferred.

The patter of the reduction electrode body 32 may be a pattern other than the patterns described in the above embodiment as long as it includes the entirety of the region corresponding to the upper layer through-holes 41b, and is not in contact with the substrate through-hole 33. Also, the pattern of the oxidation electrode body 12 may be a pattern other than the patterns demonstrated in the above embodiment as long as it includes the entirety of the region corresponding to the substrate through-holes 33.

The substrate for electrochemical measurements of the present invention enables a reactive substrate to be qualitatively determined by: bringing the oxidation electrode 12d and the reduction electrode 32d into contact with a sample solution including a redox agent such as an enzyme that oxidizes or reduced the reactive substrate, and an electronic mediator; applying a voltage to the oxidation electrode 12d and the reduction electrode 32d; and measuring the electric current that flows the oxidation electrode body 12 or the reduction electrode body 32, and further, the reactive substrate can be quantitatively determined utilizing the dependence of the electric current to the concentration of the reactive substrate.

EXAMPLES

Hereinafter, electrode plates for electrochemical measurements of Examples and Comparative Examples were manufactured, and also electrochemical determination of oxidative/reductive substance was conducted.

Electrode Body of Example 1

Figure 14:
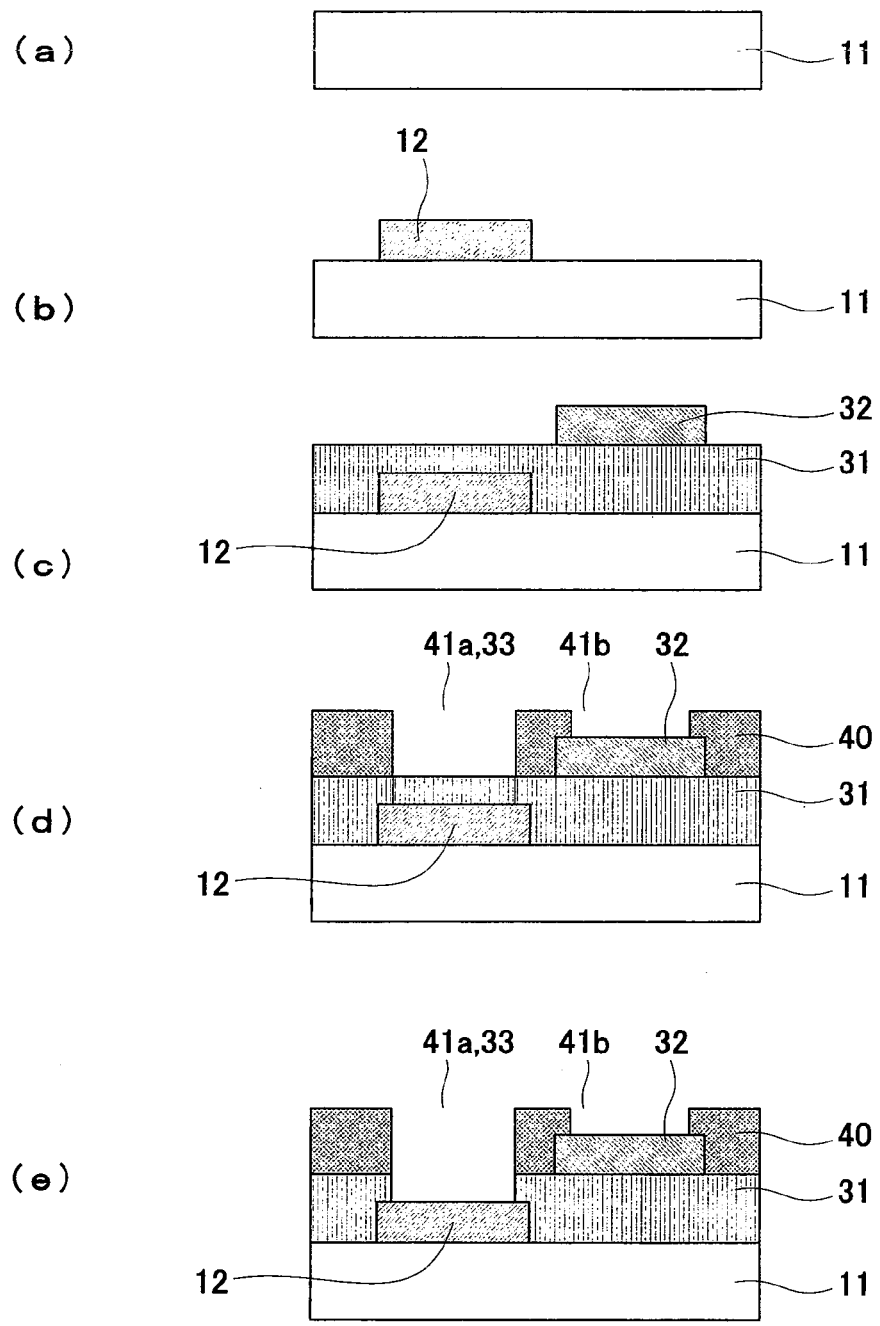
FIG. 14 shows a cross-sectional view illustrating the steps of manufacturing an electrode plate for electrochemical measurements according to Example 1.

In Example 1, the electrode plate for electrochemical measurements 1 according to the first embodiment was manufactured. The number of the upper layer through-holes 41 is different from that of the electrode plate for electrochemical measurements 1 shown in FIG. 1. FIG. 14 shows a cross-sectional view illustrating the manufacturing step of the electrode plate. First, a silicon substrate (manufactured by Shin-Etsu Chemical Co.) having a thickness of 0.5 mm with a $SiO_2$ film having a thickness of 1 μm formed on the surface thereof was used as a substrate for the lower layer 11 (FIG. 14(a)), and a lower layer film material (manufactured by Microchem Corporation: MCC PRIMER 80/20) was applied by a spin coating method thereon for improving adhesion of the resist material, followed by carrying out baking at 110° C. for 180 sec. A resist material (manufactured by Tokyo Ohka Kogyo Co., Ltd.: TSMR-8900LB) was applied thereon to give a thickness of 2 to 3 μm. This substrate was placed in an oven, and a prebaking step was carried out at 100° C. for 30 min. Next, close contact and exposure were carried out using a chromium mask with a mask aligner (manufactured by MIKASA Co., LTD) for 60 sec. Subsequently, development was carried out in a developing solution at 25° C. for 120 sec, followed by water washing, and drying to transfer the mask pattern to the resist. Thereafter, a post baking step was carried out under a condition of 120° C. for 30 min.

The substrate subjected to this resist patterning was attached to a prescribed position in a sputtering apparatus (manufactured by ULVAC, Inc.), and film formation was serially carried out with chromium, and gold. In an argon atmosphere at a pressure of 1.3 Pa, sputtering was effected with chromium for 10 sec, and with gold for 50 sec, whereby a total film thickness of 130 nm was yielded. Thereafter, the substrate was immersed in methylethyl ketone, and subjected to an ultrasonic treatment to detach the resist except for the part on which the electrode was formed. Accordingly, the oxidation electrode body 12 was obtained (FIG. 14(b)).

Next, using a plasma CVD apparatus (manufactured by ULVAC, Inc.) on the superior face of the oxidation electrode body 12, $SiO_2$ was deposited. As a result of the deposition carried out with a silane gas flow rate of 10 sccm, an $N_2O$ gas flow rate of 200 sccm, at a pressure of 80 Pa, a power of 50 W, a substrate temperature of 300° C. for 5 min, a 430 nm $SiO_2$ film was formed, whereby substrate 31 that is an insulating layer was obtained (FIG. 14(c)). A step similar to the pattern formation of the oxidation electrode body 12 was conducted thereon to obtain the reduction electrode body 32 (FIG. 14(c)).

A photosensitive resin material (manufactured by Kayaku Microchem Co., Ltd.: SU-8 2000) was applied by a spin coating method so as to have a thickness of 1 μm on the substrate surface on which the reduction electrode body 32 was formed, followed by baking at 70° C. for 30 min. Thereafter, using a chromium mask having an arrangement pattern of the upper layer through-holes 41a and 41b, exposure with close contact was carried out for 60 sec to transfer the mask pattern to the resin material. After completing the transfer, development in a developing solution was carried out at 20° C. for 300 sec, followed by water washing, and drying. Thus, a pattern of the upper layer through-holes 41b (100 μm², 10,000 holes) to allow the reduction electrode 32d to be exposed, and a pattern of the upper layer through-holes 41a (100 μm², 10,000 holes) to allow the oxidation electrode 12d to be exposed were formed on the upper layer 40 that is an insulating layer (FIG. 14(d)). The closest upper layer through-holes 41a and 41b were provided to give the distance between centers of 15 μm. Subsequently, using the transferred pattern as a mask, etching of $SiO_2$ was carried out in a reactive ion etching apparatus under conditions with a $C_2F_6$ gas flow rate of 25 sccm, at a pressure 0.25 Pa and 150 W for 15 min to obtain a pattern of substrate through-holes 33 in the substrate 31 (FIG. 14(e)). Thus formed electrode plate for electrochemical measurements 1 had a surface area of 3 mm².

According to the steps as described above, the electrode plate for electrochemical measurements of Example 1 was obtained.

Electrode Body of Comparative Example 1

Figure 15:
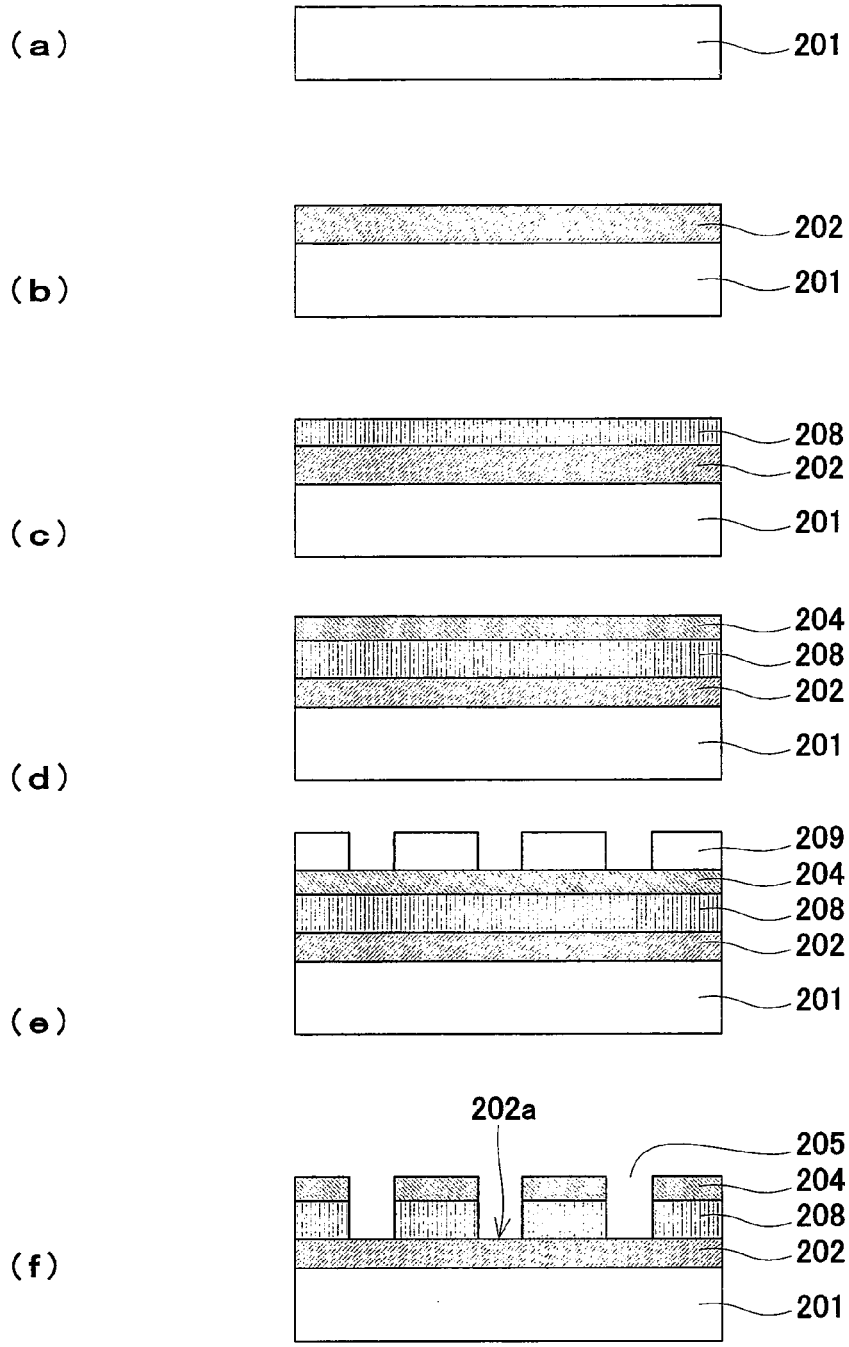
FIG. 15 shows a cross-sectional view illustrating the steps of manufacturing an electrode plate for electrochemical measurements according to Comparative Example 1.
Figure 17:
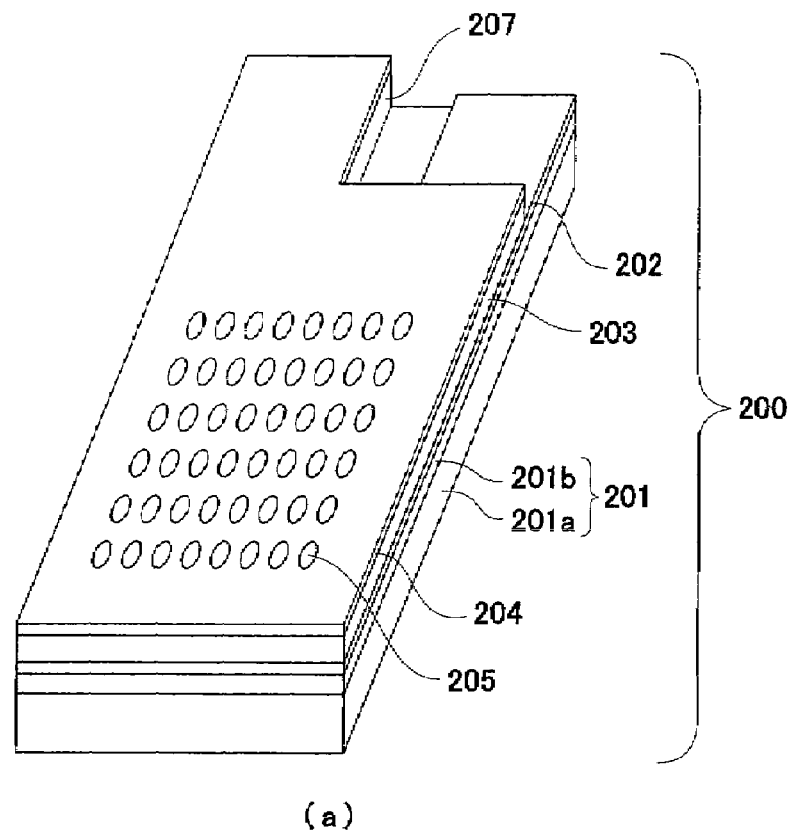
FIG. 17 shows a perspective view illustrating the construction of a conventional electrode plate for electrochemical measurements.
Figure 17:
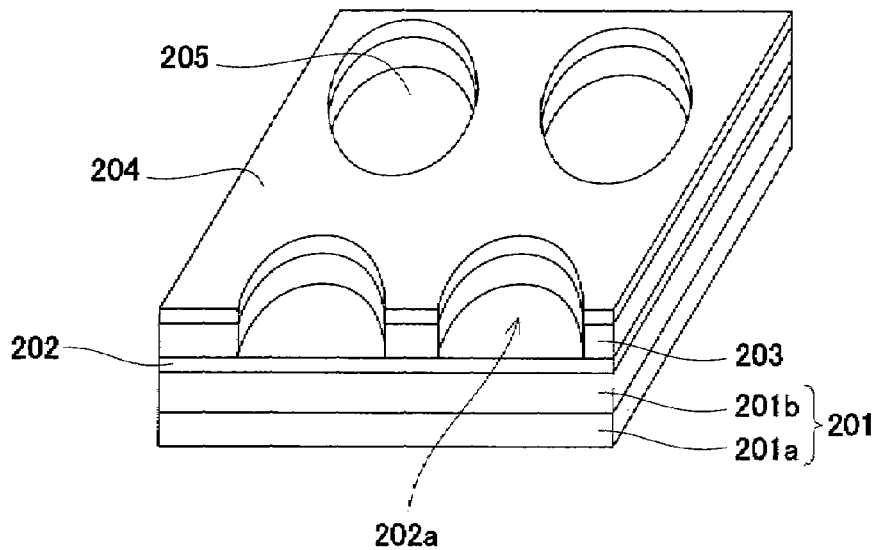

In Comparative Example 1, an electrode plate for electrochemical measurements having a conventional structure shown in FIG. 17 was manufactured. FIG. 15 shows a cross-sectional view illustrating the manufacturing step of the electrode body of Comparative Example 1. A silicon substrate (manufactured by Shin-Etsu Chemical Co.) having a thickness of 0.5 mm with a $SiO_2$ film having a thickness of 1 μm formed on the surface thereof was used as substrate 201 shown in FIG. 15(a), which was attached to a prescribed position in a sputtering apparatus (manufactured by ULVAC, Inc.), and then the metal mask was set thereto. Thereafter, film formation was serially carried out with chromium, and gold. The bottom electrode body 202 was then obtained by sputtering in an argon atmosphere at a pressure of 1.3 Pa with chromium for 10 sec, and with gold for 50 sec to give a total film thickness of 130 nm (FIG. 15(b)). Next, the metal mask was removed, and $SiO_2$ was deposited as an insulating film on the upper layer of the bottom electrode body 202 using a plasma CVD apparatus (manufactured by ULVAC, Inc.). Under sputtering conditions with a silane gas flow rate of 10 sccm, and $N_2O$ gas flow rate 200 sccm, at pressure 80 Pa and power 50 W, a substrate temperature of 300° C., deposition was carried out for 5 min. As a result, a 430 nm $SiO_2$ film was formed to obtain an insulating layer 208 (FIG. 15(c)).

Another metal mask was placed thereon, a chromium-platinum film was formed to give a thickness of 130 nm under conditions similar to those in forming the bottom electrode body 202, whereby surface electrode 204 was formed (FIG. 15(d)). Next, a resist material (manufactured by Tokyo Ohka Kogyo Co., Ltd.: TSMR-8900LB) was applied on the substrate to give a thickness of 2 to 3 μm. This substrate following application and film formation of the resist was placed in an oven, and a prebaking step was carried out at 100° C. for 30 min. Thereafter, close contact and exposure were carried out using a chromium mask with a mask aligner (manufactured by MIKASA Co., LTD) for 60 sec. Subsequently, development was carried out in a developing solution at 25° C. for 120 sec, followed by water washing, and drying to transfer the mask pattern to the resist 209 (FIG. 15(e)). The post baking step was carried out under a condition of 120° C. for 30 min.

The substrate having the resist 209 on which the mask pattern produced previously was transferred, was placed in an argon milling apparatus, and etching was serially carried out under conditions with an argon gas flow rate of 12 sccm, at a pressure of 0.03 Pa, and a beam electric current of 90 mA with gold, and with chromium. Thus etched substrate was placed in a reactive ion etching apparatus, and etching was carried out again with $SiO_2$ under conditions with a $C_2F_6$ gas flow rate of 25 sccm, at a pressure of 0.25 Pa, and at 150 W for 15 min. As a result, an electrode plate having a large number of micropores 205 exposed at the bottom face in a part of the bottom electrode body 202 (hereinafter, oxidation electrode 202a) was obtained. Thus formed micropores 205 had an area of 100 μm², in the number of 10,000, and the distance between centers was 110 μm. Also, the surface electrode 204 formed had an area of 300 mm².

Electrochemical Measurement Using Electrode Plate for Electrochemical Measurements of Example 1 and Comparative Example 1

Apparatuses for electrochemical measurements were constructed using the electrode plate for electrochemical measurements produced in Example 1, and the electrode plate for electrochemical measurements produced in Comparative Example 1, and the response electric current of an electronic mediator was measured. In the apparatus for electrochemical measurements, the oxidation electrode 12d and the reduction electrode 32d (oxidation electrode 202a and surface electrode 204 in Comparative Example 1) were constructed so as to be exposed to the sample solution. As the electronic mediator, 1 mmol/l potassium ferrocyanide and 1 mmol/l potassium ferricyanide 1 mmol/l (2 mmol/l in total) were dissolved in an aqueous 50 mmol/l supporting electrolyte (potassium chloride) solution, which was used for a sample solution. The reference electrode employed was a silver/silver chloride electrode (manufactured by BAS Inc.). A platinum wire was used as the auxiliary electrode.

The electrode plate for electrochemical measurements of Example 1 was connected to Bipotentiostat (manufactured by CH instruments, Inc.: ALS740A) via a lead wire, and then the reaction electric current that flows the oxidation electrode 12d was measured by cyclic voltammetry with setting of: the potential of the oxidation electrode 12d with respect to the reference electrode being 0 to +0.7 V; the potential of the reduction electrode 32d being 0 V; and the sweeping rate of the potential being 100 mV/s.

In addition, the electrode plate for electrochemical measurements of Comparative Example 1 was similarly connected to Bipotentiostat via a lead wire, and sweeping was carried out onto the silver/silver chloride electrode with the potential of the oxidation electrode 202a as a reference electrode, from 0 to +0.7 V at a sweeping rate of 100 mV/s. In this procedure, the potential of the surface electrode 204 was set to 0 V with respect to the reference electrode.

As a result, in the electrode plate for electrochemical measurements of Comparative Example 1, the stationary electric current accompanying with the oxidative reaction of potassium ferrocyanide was observed at the potential of the oxidation electrode 202a being from +0.6 to +0.7 V, with the value of 15.1 μA at +0.7 V. The oxidative reaction formula of potassium ferrocyanide is as represented by the following formula 1.

Formula 1:

$$Fe(CN)_6^{-4} \rightarrow Fe(CN)_6^{-3} + e^- \qquad (\text{formula 1})$$

Meanwhile, also in the electrode plate for electrochemical measurements of Example 1, the stationary electric current associated with the oxidative reaction of potassium ferrocyanide was observed at the potential of the oxidation electrode 12*d* being from +0.6 to +0.7 V, with the value of 39.1 μA at +0.7 V. The greater electric current value was observed in Example 1 as compared to the value with the electrode plate for electrochemical measurements of Comparative Example 1 because, taking into consideration the explanatory view of the self-induced redox cycle shown in FIG. 18, the electric current of the oxidative reaction is believed to be increased since potassium ferrocyanide oxidized on the surface electrode 204 (macroelectrode 222) in Comparative Example 1 was efficiently oxidized on the reduction electrode 32*d* (fine electrode 221) in Example 1. Thus, in the electrode plate for electrochemical measurements of this Example, a large number of fine electrode pairs having the same shape and area are arranged on the substrate, therefore, uniform reaction area between respective two electrode pairs can be provided, and thus an efficient redox cycle reaction is believed to proceed between the two poles.

In addition, with respect to the oxidation electrode 202*a* of Comparative Example 1, and the oxidation electrode 12*d* of Example 1, time dependency of the oxidation electric current yielded by rapidly sweeping the potential up to natural potential of +0.4 V was evaluated. During this evaluation, the potential of the surface electrode 204 of Comparative Example 1 and the reduction electrode 32*d* of Example 1 was kept at 0 V. As a result, a time period of 26 sec was required until the electric current of the oxidation electrode 202*a* of Comparative Example 1 reached the stationary state, while the oxidation electrode 12*d* of Example 1 reached the stationary state in 6 sec. This would suggest that the oxidation electrode 202*a* of Comparative Example 1 needed a long period of time for achieving the stationary state of the surface electrode 204, but in contrast, the oxidation electrode 12*d* of Example 1 promptly reached the stationary state between the electrode pairs having the same area and shape.

From the results described above, it was proven that the electrode plate for electrochemical measurements of Example 1 enables quick determination with high sensitivity.

Electrode Plate for Electrochemical Measurements of Example 2

In Example 2, the electrode plate for electrochemical measurements according to the second embodiment having each pore with a cross-sectional shape of regular hexagon was manufactured. The method for production was similar to that in Example 1 except only that sputtering was employed in place of the plasma CVD used for forming the substrate 31 in Example 1.

A substrate on which the oxidation electrode body 12 was formed was attached to a prescribed position in a sputtering apparatus (manufactured by ULVAC, Inc.), deposition was carried out with an oxygen gas flow rate of 5 sccm, an argon gas flow rate of 5 sccm, at a pressure of 0.3 Pa, a power of 500 W, an anode electric current of 0.35 A, and an anode voltage of 2.21 kV, with the distance between the target and the substrate being 50 mm for 25 min to form substrate 31. In the subsequent procedure, similar steps to those in Example 1 were carried out to apply a photosensitive resin material to the substrate surface on which the reduction electrode body 32 was formed. Next, the mask pattern having a pattern of regular hexagonal pores was transferred to the photosensitive resin material. A step of forming the upper layer through-hole 41 and the substrate through-hole 33 was carried out, whereby the electrode plate for electrochemical measurements of this Example was obtained. Each pore had an area of 21.7 μm², and the number of the upper layer through-holes 41*b* for exposing the reduction electrode 32*d*, and the number of the upper layer through-holes 41*a* to allow the oxidation electrode 12*d* to be exposed were both 10,000. The upper layer through-holes 41*a* were formed to get the closest to the four upper layer through-holes 41*b*, with the distance between centers being 15 μm. Similarly, the upper layer through-holes 41*b* were formed to get the closest to the four upper layer through-holes 41*a*, with the distance between centers being 15 μm.

Electrochemical Measurement Using Electrode Plate for Electrochemical measurements of Example 2

Next, an apparatus for electrochemical measurements was constructed using the electrode plate for electrochemical measurements of Example 2 under similar conditions to Example 1, and the oxidation electric current of potassium ferrocyanide was determined, which was compared to the measurement results of the electrode plate for electrochemical measurements demonstrated in Comparative Example 1. In the electrode plate for electrochemical measurements of this Example, sweeping was carried out onto the silver/silver chloride electrode with the potential of the bottom electrode 12 of from 0 to +0.7 V. Accordingly, the stationary electric current of the potassium ferrocyanide oxidative reaction was observed over +0.6 to +0.7 V, with the value of 40.8 μA at +0.7 V. In the electrode plate for electrochemical measurements of this Example, stationary electric current was obtained 10 sec after starting the reaction.

From the results described above, it was proven that the electrode plate for electrochemical measurements of Example 2 also enables quick determination with high sensitivity similarly to the electrode plate for electrochemical measurements of Example 1.

Electrode Plate for Electrochemical Measurements of Example 3

Figure 16:
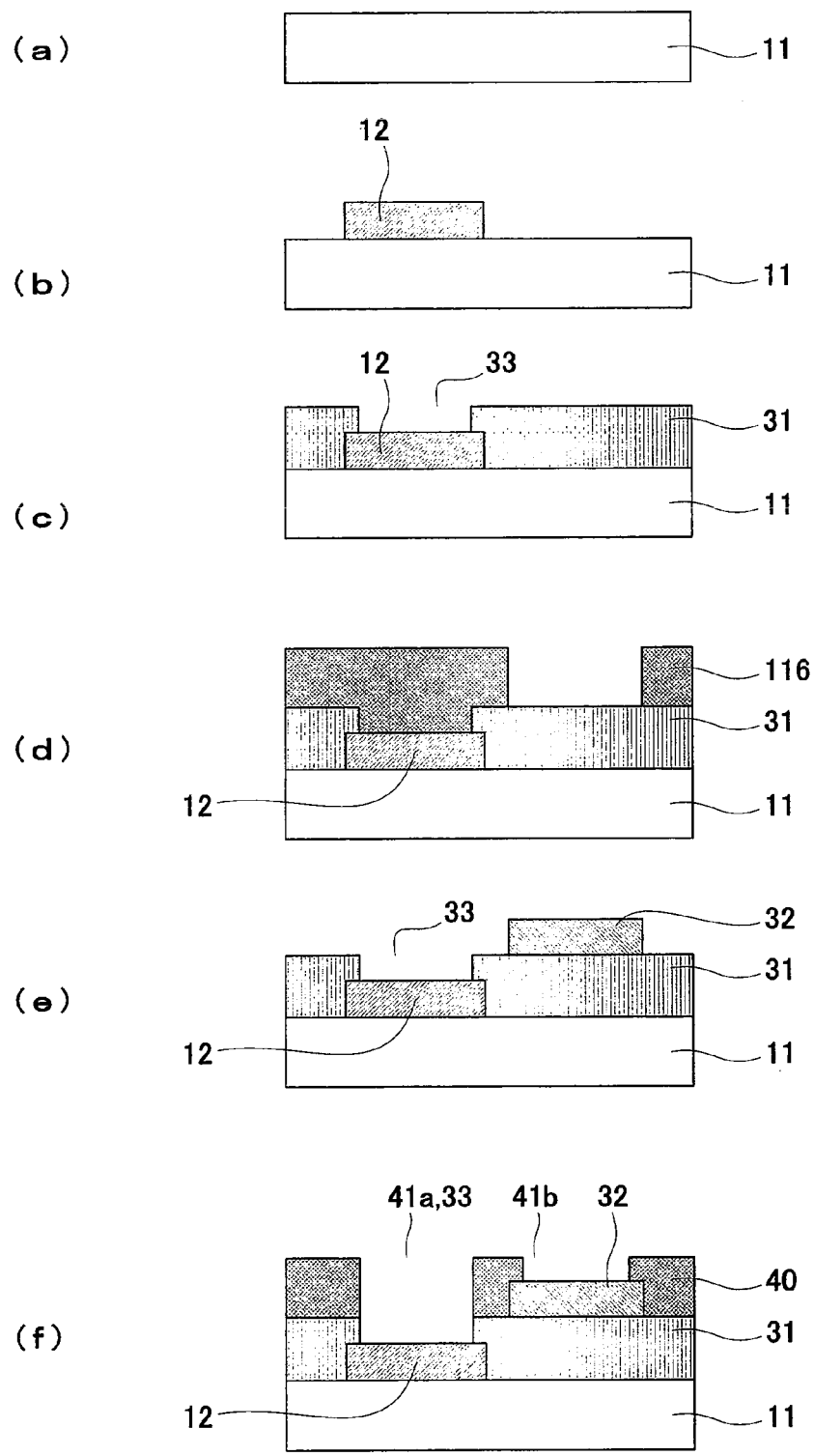
FIG. 16 shows a cross-sectional view illustrating the steps of manufacturing an electrode plate for electrochemical measurements according to Example 3.

The construction of the electrode plate for electrochemical measurements of Example 3 is similar to the construction of the electrode plate for electrochemical measurements of Example 1. Although an SiO₂ layer was employed in forming the substrate 31 in Example 1, a photosensitive resin layer was used instead in this Example. Hereafter, method for production of the electrode plate for electrochemical measurements of this Example is explained. FIG. 16 shows a cross-sectional view illustrating the manufacturing step of the electrode plate for electrochemical measurements of Example 3. A substrate to serve as the lower layer 11 was provided (FIG. 16(*a*)), and the oxidation electrode body 12 was formed on the lower layer 11 by a similar procedure to Example 1 (FIG. 16(*b*)). Onto the lower layer 11 was applied a photosensitive resin material (manufactured by Kayaku Microchem Co., Ltd.: SU-8 2000) to give a thickness of 430 nm, followed by baking at 70° C. for 25 min baking. Thereafter, a mask pattern was transferred to the resin material using a chromium mask having a pattern with substrate through-holes 33 for exposing the oxidation electrode 12*d*. Following the transfer, development was carried out in a developing solution at 20° C. for 300 sec, followed by water washing, and drying to form substrate 31 having substrate through-holes 33 (100 µm², 1,000 holes) (FIG. 16(c)). The same type of a resist material as that of Example 1 was applied thereon to give a thickness of 2 µm, and a baking step was carried out. Using a mask having a pattern of the reduction electrode body 32, the pattern of the reduction electrode body 32 was transferred. Thereafter, washing and drying steps were carried out to form resist 116 having the pattern on the reduction electrode body 32 (FIG. 16(d)). Next, titanium and gold films were formed under similar conditions to those in Example 1, and thus reduction electrode body 32 was obtained by a lift off process (FIG. 16(e)). A photosensitive resin material which is the same as that of the substrate 31 was applied thereon to give a thickness of 1 µm by spin coating, followed by baking at 70° C. for 30 min to form upper layer 40. Thereafter, using a chromium mask having a pattern of the upper layer through-hole 41a to allow the oxidation electrode 12d to be exposed, and the upper layer through-hole 41b to allow the reduction electrode 32d to be exposed, exposure with close contact was carried out for 60 sec to transfer the mask pattern to the resin material. After completing the transfer, development in a developing solution was carried out at 20° C. for 420 sec, followed by water washing, and drying to obtain upper layer through-holes 41b (100 µm², 10,000 holes). In addition, upper layer through-holes 41a (100 µm², 10,000 holes) were formed in the upper layer 40, and pores having the same shape were formed in the substrate 31. Thus, through-holes that are continuous from the upper layer 40 to the substrate 31 were formed. The distance between centers of upper layer through-holes 41a and the upper layer through-holes 41b adjacent in the lengthwise direction and the lateral direction was set to be 15 µm. Accordingly, the electrode plate for electrochemical measurements of this Example was obtained (FIG. 16(f)).

Electrochemical Measurement Using Electrode Plate for Electrochemical Measurements of Example 3

Next, an apparatus for electrochemical measurements was constructed using the electrode plate for electrochemical measurements of Example 3 under similar conditions to the measurement in Example 1, and the oxidation electric current of potassium ferrocyanide was determined. In the electrode plate for electrochemical measurements of Example 3, sweeping was carried out onto the silver/silver chloride electrode with the potential of the oxidation electrode body 12 of from 0 to +0.7 V. Accordingly, the stationary electric current of the potassium ferrocyanide oxidative reaction was observed over +0.6 to +0.7 V, with the value of 39.1 µA at +0.7 V. In the electrode plate for electrochemical measurements of this Example, stationary electric current was obtained 7 sec after starting the reaction. From the results described above, it was proven that the electrode plate for electrochemical measurements of Example 3 also enables quick determination with high sensitivity similarly to the electrode plate for electrochemical measurements of Example 1.

From the foregoing description, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

The electrode plate for electrochemical measurements according to the present invention can be utilized in apparatuses for electrochemical measurements for quantitatively determining substances included in biological samples in a slight amount such as sucrose, glucose and the like. In addition, the electrode plate for electrochemical measurements according to the present invention can be also utilized in apparatuses for electrochemical measurements such as electrochemical sensors and detectors of liquid chromatograms for determining the concentration of toxic substances included in drinking water and the like.

What is claimed is:

1. An electrode plate for electrochemical measurements comprising
   a substrate made of an insulator,
   an upper layer made of an insulator provided on an upper face of the substrate,
   a lower layer made of an insulator provided on a lower face of the substrate,
   a first electrode body sandwiched between the upper face of the substrate and the upper layer, and
   a second electrode body sandwiched between the lower face of the substrate and the lower layer, wherein:
   the upper layer has a plurality of upper layer through-holes;
   the first electrode body has a plurality of first electrodes comprising a portion exposed from an upper face of the upper layer via the upper layer through-hole in the first electrode body;
   the substrate has a plurality of substrate through-holes; and
   the second electrode body has a plurality of second electrodes comprising a portion exposed from the upper face of the upper layer via the upper layer through-hole and the substrate through-hole in the second electrode body in the second electrode body, and wherein:
   on a plane view,
   any of the plurality of substrate through-holes does not overlap with the first electrode body;
   four second electrodes are disposed around the each first electrode, with an even distance between centers of the first electrode and the second electrode;
   four first electrodes are disposed around the each second electrode, with an even distance between centers of the second electrode and the first electrode,
   an area of the each first electrode is all substantially the same as an area of the each second electrode.

2. The electrode plate for electrochemical measurements according to claim 1, wherein the first electrode body comprises a plurality of branches that form zigzag extended such that the first electrodes are serially linked, and a stem to which one end of the plurality of branches is connected.

3. The electrode plate for electrochemical measurements according to claim 1, wherein the second electrode body comprises a plurality of branches that form zigzag extended such that the second electrodes are serially linked, and a stem to which one end of the plurality of branches is connected.

4. The electrode plate for electrochemical measurements according to claim 1, wherein the first electrode body is constituted with a metal plate having a plurality of cut-part formed by cutting off to be slightly larger than regions corresponding to the plurality of substrate through-holes.

5. The electrode plate for electrochemical measurements according to claim 1, wherein the second electrode body is constituted with a metal plate including all the plurality of second electrodes.

6. The electrode plate for electrochemical measurements according to claim 1, wherein a cross sectional area of the each upper layer through-hole is substantially the same as the area of the each first electrode, and a cross sectional area of the each substrate through-hole is substantially the same as the area of the each second electrode.

7. The electrode plate for electrochemical measurements according to claim 1, wherein a cross-sectional shape of the each upper layer through-hole and a cross-sectional shape of the each substrate through-hole are a square.

8. The electrode plate for electrochemical measurements according to claim 1, wherein a cross-sectional shape of the each upper layer through-hole and a cross-sectional shape of the each substrate through-hole are a regular hexagon.

9. An apparatus for electrochemical measurements comprising a reference electrode, an auxiliary electrode and an electrode plate for electrochemical measurements, or a counter electrode and an electrode plate for electrochemical measurements, the electrode plate for electrochemical measurements comprising
a substrate made of an insulator,
an upper layer made of an insulator provided on an upper face of the substrate,
a lower layer made of an insulator provided on a lower face of the substrate,
a first electrode body sandwiched between the upper face of the substrate and the upper layer, and
a second electrode body sandwiched between the lower face of the substrate and the lower layer, wherein:
the upper layer has a plurality of upper layer through-holes;
the first electrode body has a plurality of first electrodes comprising a portion exposed from an upper face of the upper layer via the upper layer through-hole in the first electrode body;
the substrate has a plurality of substrate through-holes; and
the second electrode body has a plurality of second electrodes comprising a portion exposed from the upper face of the upper layer via the upper layer through-hole and the substrate through-hole in the second electrode body in the second electrode body, and wherein:
on a plane view,
any of the plurality of substrate through-holes does not overlap with the first electrode body;
four second electrodes are disposed around the each first electrode, with an even distance between centers of the first electrode and the second electrode;
four first electrodes are disposed around the each second electrode, with an even distance between centers of the second electrode and the first electrode,
an area of the each first electrode is all substantially the same as an area of the each second electrode.

10. The apparatus for electrochemical measurements according to claim 9, wherein the first electrode body comprises a plurality of branches that form zigzag extended such that the first electrodes are serially linked, and a stem to which one end of the plurality of branches is connected.

11. The apparatus for electrochemical measurements according to claim 9, wherein the second electrode body comprises a plurality of branches that form zigzag extended such that the second electrodes are serially linked, and a stem to which one end of the plurality of branches is connected.

12. The apparatus for electrochemical measurements according to claim 9, wherein the first electrode body is constituted with a metal plate having a plurality of cut-part formed by cutting off to be slightly larger than regions corresponding to the plurality of substrate through-holes.

13. The apparatus for electrochemical measurements according to claim 9, wherein the second electrode body is constituted with a metal plate including all the plurality of second electrodes.

14. The apparatus for electrochemical measurements according to claim 9, wherein a cross sectional area of the each upper layer through-hole is substantially the same as the area of the each first electrode, and a cross sectional area of the each substrate through-hole is substantially the same as the area of the each second electrode.

15. The apparatus for electrochemical measurements according to claim 9, wherein a cross-sectional shape of the each upper layer through-hole and a cross-sectional shape of the each substrate through-hole are a square.

16. The apparatus for electrochemical measurements according to claim 9, wherein a cross-sectional shape of the each upper layer through-hole and a cross-sectional shape of the each substrate through-hole are a regular hexagon.

17. A method of the quantitative determination of a target substance included in a sample solution with an apparatus for electrochemical measurements comprising a reference electrode, an auxiliary electrode and an electrode plate for electrochemical measurements, or a counter electrode and an electrode plate for electrochemical measurements,
the sample solution comprising an electronic mediator,
the electrode plate for electrochemical measurements comprising
a substrate made of an insulator,
an upper layer made of an insulator provided on an upper face of the substrate,
a lower layer made of an insulator provided on a lower face of the substrate,
a first electrode body sandwiched between the upper face of the substrate and the upper layer, and
a second electrode body sandwiched between the lower face of the substrate and the lower layer, wherein:
the upper layer has a plurality of upper layer through-holes;
the first electrode body has a plurality of first electrodes comprising a portion exposed from an upper face of the upper layer via the upper layer through-hole in the first electrode body;
the substrate has a plurality of substrate through-holes; and
the second electrode body has a plurality of second electrodes comprising a portion exposed from the upper face of the upper layer via the upper layer through-hole and the substrate through-hole in the second electrode body in the second electrode body, and wherein:
on a plane view,
any of the plurality of substrate through-holes does not overlap with the first electrode body;
four second electrodes are disposed around the each first electrode, with an even distance between centers of the first electrode and the second electrode;
four first electrodes are disposed around the each second electrode, with an even distance between centers of the second electrode and the first electrode,
an area of the each first electrode is all substantially the same as an area of the each second electrode, and
the method comprising the steps of:
bringing the reference electrode, the auxiliary electrode, and the electrode plate for electrochemical measurements, or the counter electrode and the electrode plate for electrochemical measurements into contact with the sample solution;
measuring the electric current by sweeping a positive potential to either one of the first electrode body and the second electrode body, and applying a negative potential to another one, or applying a positive potential to either one of the first electrode body and the second electrode body, and sweeping a negative potential to another one, thereby determining the electric current that flows between the first electrode body and the second electrode body; and calculating the amount of the target substance from the electric current derived in the step of measuring the electric current.

18. The method according to claim 17, wherein the first electrode body comprises a plurality of branches that form zigzag extended such that the first electrodes are serially linked, and a stem to which one end of the plurality of branches is connected.

19. The method according to claim 17, wherein the second electrode body comprises a plurality of branches that form zigzag extended such that the second electrodes are serially linked, and a stem to which one end of the plurality of branches is connected.

20. The method according to claim 17, wherein the first electrode body is constituted with a metal plate having a plurality of cut-part formed by cutting off to be slightly larger than regions corresponding to the plurality of substrate through-holes.

21. The method according to claim 17, wherein the second electrode body is constituted with a metal plate including all the plurality of second electrodes.

22. The method according to claim 17, wherein a cross sectional area of the each upper layer through-hole is substantially the same as the area of the each first electrode, and a cross sectional area of the each substrate through-hole is substantially the same as the area of the each second electrode.

23. The method according to claim 17, wherein a cross-sectional shape of the each upper layer through-hole and a cross-sectional shape of the each substrate through-hole are a square.

24. The method according to claim 17, wherein a cross-sectional shape of the each upper layer through-hole and a cross-sectional shape of the each substrate through-hole are a regular hexagon.

* * * * *